US006972129B1

(12) United States Patent
Ogawa et al.

(10) Patent No.: US 6,972,129 B1
(45) Date of Patent: Dec. 6, 2005

(54) METHOD FOR PRODUCING COSMETICS

(75) Inventors: Katsuki Ogawa, Kanagawa (JP); Kazuhisa Ohno, Kanagawa (JP); Akio Nasu, Kanagawa (JP); Kyoko Joichi, Kanagawa (JP); Hiroshi Fukui, Kanagawa (JP); Hideo Hata, Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 38 days.

(21) Appl. No.: 09/889,826

(22) PCT Filed: Nov. 27, 2000

(86) PCT No.: PCT/JP00/08328

§ 371 (c)(1),
(2), (4) Date: Jul. 23, 2001

(87) PCT Pub. No.: WO01/37795

PCT Pub. Date: May 31, 2001

(30) Foreign Application Priority Data

| Nov. 25, 1999 | (JP) | ................................. 11-334101 |
| Jan. 6, 2000 | (JP) | ........................... 2000-000890 |
| Jan. 6, 2000 | (JP) | ........................... 2000-000891 |

(51) Int. Cl.[7] .......................... A61K 7/00; A61K 9/50; A61K 7/42
(52) U.S. Cl. ..................... 424/401; 424/492; 424/489; 424/59; 424/64; 514/769; 514/770; 514/844; 514/944; 514/937; 106/412
(58) Field of Search .............................. 424/401, 492, 424/489, 59, 64, DIG. 5, 63, 70.9; 106/412; 514/769, 770, 844, 944, 937

(56) References Cited

U.S. PATENT DOCUMENTS 5,957,398 A * 9/1999 Ogata et al. .................. 241/27

FOREIGN PATENT DOCUMENTS

| EP | 0 546 715 A1 | 6/1993 |
| WO | WO98/16193 | 8/1997 |

OTHER PUBLICATIONS

Sunstar Inc., Tayca Corporation, Machine Assisted Translation of JP9-286713 A, Nov. 4, 1997, See: entire reference.*
Futamata et al., Ishihara Sangyo Co., Translation of WO 98/16193, Apr. 23, 1998, See: entire reference.*
Japanese Patent Office, Patent Abstracts of Japan, Publication No.: 09-208438, Date of Publication: Aug. 12, 1997, Application No.: 08-289132, Date of Filing: Oct. 11, 1996, English Abstract Only.
Japanese Patent Office, Patent Abstracts of Japan, Publication No.: 09-002816, Date of Publication: Jan. 7, 1997, Application No.: 07-156020, Date of Filing: Jun. 22, 1995, English Abstract Only.
Japanese Patent Office, Patent Abstracts of Japan, Publication No.: 09-002815, Date of Publication: Jan. 7, 1997, Application No.: 07-156019, Date of Filing: Jun. 22, 1995, English Abstract Only.
Japanese Patent Office, Patent Abstracts of Japan, Publication No.: 09-286713, Date of Publication: Nov. 4, 1997, Application No.: 08-096574, Date of Filing: Apr. 18, 1996, English Abstract Only.

* cited by examiner

Primary Examiner—Vickie Kim
(74) Attorney, Agent, or Firm—Snider & Associates; Ronald R. Snider

(57) ABSTRACT

An objective of the present invention is to provide a method for producing cosmetic products capable of improving a touch of cosmetic products containing powder and exerting the function of the powder sufficiently. In order to accomplish the objective described above, a method for producing cosmetic products according to the invention comprises a use of a media-agitating mill to disperse powder components and oil components or aqueous components. A method for producing cosmetic products according to the invention is applied to powdery cosmetic products, oily cosmetic products, emulsified cosmetic products and lipsticks. A method for producing cosmetic products involving a step for imparting a particle with hydrophobicity using a media-agitating mill is also provided. Furthermore, a method for producing cosmetic products using hydrophobicity-imparted powdery dispersion containing organically-denatured clay mineral is provided.

25 Claims, 2 Drawing Sheets

F I G. 1
(A)
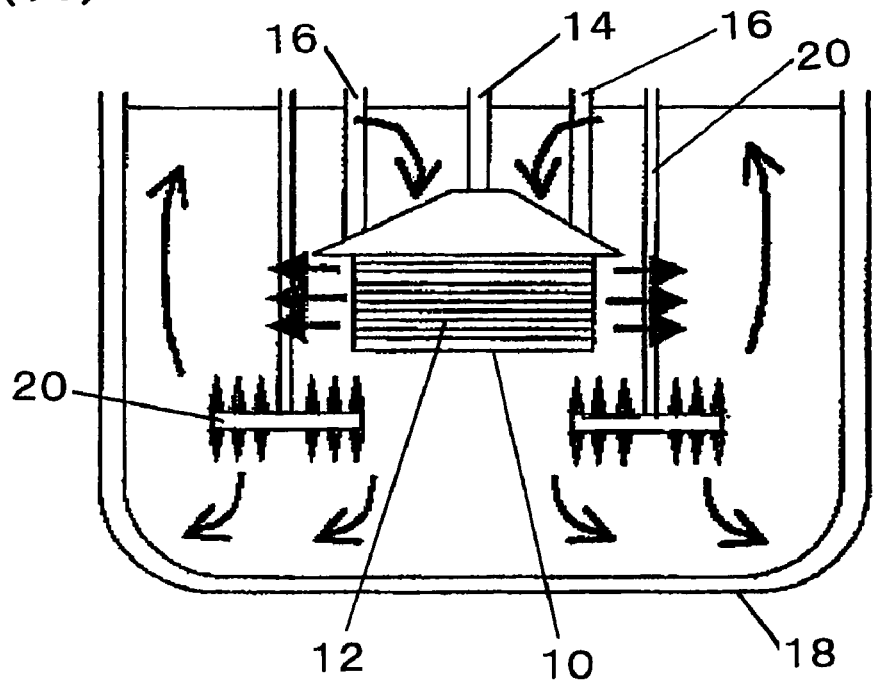
(B)
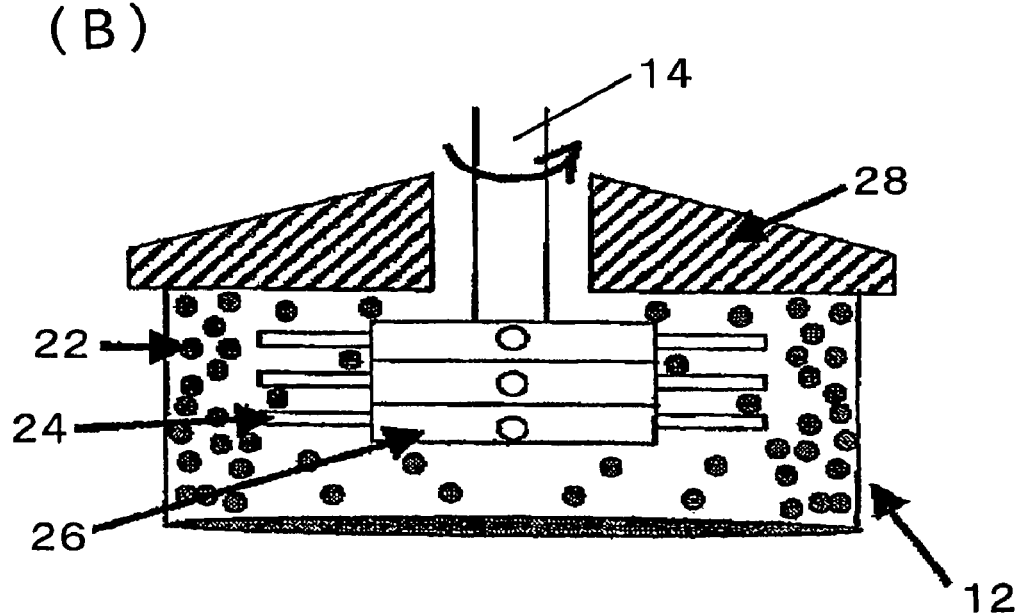

F I G 2
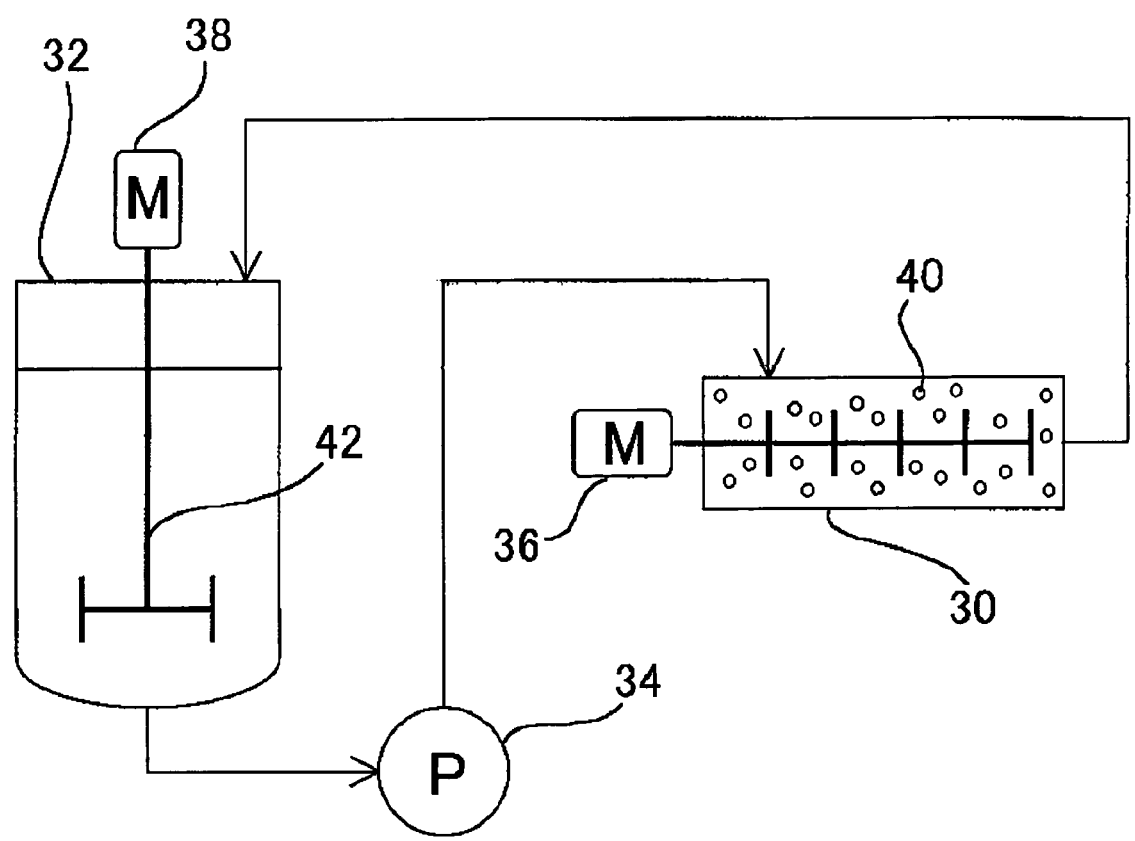

METHOD FOR PRODUCING COSMETICS

RELATED APPLICATIONS

This application claims the priorities of Japanese Patent Application No. 11-334101 filed on Nov. 25, 1999, Japanese Patent Application No. 2000-890 filed on Jan. 6, 2000 and Japanese Patent Application No. 2000-891 filed on Jan. 6, 2000 which are incorporated herein by reference. Applicant also claims priority of PCT/JP00/08328.

FIELD OF THE INVENTION

The present invention relates to a method for producing cosmetic products, especially to a method for producing cosmetic products which improves the function and the touch of powder contained in the cosmetic product.

BACKGROUND OF THE INVENTION

As representative cosmetic products containing powder, a foundation, a sunscreen or a lipstick may be exemplified. Cosmetic products containing such powder can be classified, based on the production method, into powdery cosmetic products, oily cosmetic products or emulsified cosmetic products. As a conventional method for improving the function of powder, an incorporation of a hydrophobicity-imparting agent is employed. However, a conventional method for producing cosmetic products involves a difficulty in utilizing the function of powder incorporated sufficiently. In addition, solid cosmetic products are also disadvantage experienced as a susceptibility to impact and a tendency of being broken easily. Furthermore, a conventional powder-containing cosmetic product may exhibit a dusty skin feel, resulting in a poor touch. A technical background of each cosmetic product is discussed below.

Powdery Cosmetic Products

A powdery cosmetic product is a cosmetic product obtained by filling a starting material consisting of powder components as a major constituent admixed with oil components as binders and surfactants into a metal or resin inner canister, and optionally a subsequent press molding step. Generally, powdery cosmetic products are used with cosmetic tools such as a puff, a sponge and a brush.

A powdery cosmetic product has conventionally been produced by using an agitating mixer such as Henschel mixer, nautor mixer, ribbon blender, kneader and the like to mix powder components and oil components as binders and surfactants followed by grinding using a grinder such as pulverizer followed by filling into a metal or resin inner canister optionally followed by a dry press molding.

Recently, A powdery cosmetic product is subjected to an extensive development with regard to production and molding methods for the purpose of improving its practical characteristics such as the touch. For example, a filling-solidifying method (Japanese Patent No. 1556592) wherein a cosmetic base is mixed with solvent such as alcohol to form a slurry which is then filled in a container, and subsequently the solvent is removed with suction under vacuum to produce cosmetic products or a method for producing a solid powdery makeup product (JP-A-7-277924) incorporating a certain powder as powder component are proposed.

Nevertheless, a diverse and sophisticated demand by consumers in these days raises a further need to improve the practical characteristics and the impact resistance.

On the other hand, for the purpose of improving the long-lasting performance of a makeup against sweat or sebum or enabling the use of water especially in the field of a powdery foundation, an incorporation of a particle whose surface is imparted with a hydrophobicity was attempted to produce a two-way summer foundation.

However, such two-way foundation which employs a particle whose surface has previously been imparted with hydrophobicity using silicone and the like is problematically time-consuming and economically disadvantageous since it requires such hydrophobicity imparting treatment for the particle in addition to the foundation producing process.

Oily Cosmetic Product and Emulsified Cosmetic Product

In an ordinary method for producing an oily cosmetic product, a colorant containing a particle is mixed with oil components using a roll mill or equivalent, and the aggregated particle was dispersed to a level of a primary particle to obtain a paste, which is admixed into a molten mixture of a solidifying agent and other oil components, and the mixture is agitated using a disper or equivalent, filled in a container, and then molded. In another method for producing an oily cosmetic product, a particle mass is ground preliminarily using a grinder such as a pulverizer and mixed with oil components using a disper or equivalent, and, in a case of a stick-type cosmetic product, admixed into a melted mixture of a solidifying agent and an oily agent and mixed using a disper or equivalent, and then filled and molded.

However, when an oily cosmetic product is produced by a method described above, the production cost and the production time become problematic since a preliminary roll milling process or a pulverizer grinding process is required. A roll milling process requires a well-trained skill and involves a difficulty in being applied to a mass production. In addition, particulate powder having a large specific surface area, when incorporated, requires a substantially reduced powder ratio for effecting a roll milling process. Accordingly, a particulate iron oxide, which is known to be transparent excellently and has a UV-protecting effect, can not practically be incorporated. In addition, a pulverizer process poses a poor operating environment, and results in an insufficient grinding or dispersing of a particulate titanium oxide or a particulate zinc oxide which is incorporated into an oily foundation for the purpose of imparting a UV-protecting effect. Moreover, a difficulty is also experienced in obtaining a UV-protecting effect expected from the amount incorporated, thus the suitability to a method for producing cosmetic products incorporating particulate powder being absent eventually. Also since the incorporation of a particulate iron oxide which is expected to impart a UV-protecting effect is not suitable because of the same reason, it is not performed actually.

Existing studies on emulsified cosmetic products include a method for producing a dispersion of a particulate titanium oxide (JP-A-9-208438), an oil dispersion and a method for producing the same (Japanese Patent Registration No. 6-61457) and a satisfactorily dispersible composition and cosmetic products containing the same (JP-A-10-167946), any of which employs a circulatory media mill utilizing a pipe and a motor, which is called a lateral continuous sand mill.

However, such dispersion, when incorporated into a sunscreen or an emulsified foundation, is disadvantageous in terms of the supply and the cost of the dispersion and involves a limitation of time period until the production of the dispersion, resulting in a difficulty in being incorporated readily.

Accordingly, a process of manufacturing in which the processes from the formation of a dispersion through the formation of an emulsified cosmetic product is conducted at once. However, a circulatory sand mill described above can disperse powder into an oily agent but does not involve a step for adding an water phase, resulting in an impossibility of emulsifying. In addition, a media mill of this type requires a preliminary mixer separately in addition to a dispersing device, exerts a similarly strong mechanical force for dispersing which is not suitable to the production of an emulsified cosmetic product to which various types of the particles are incorporated, and also employs a preliminary agitating device and a circulation pipe in addition to a dispersing device which leads to a difficulty in washing, thus presenting problematic characteristics.

A composition such as cosmetic products usually contains a particle such as a particulate titanium oxide or a particulate zinc oxide. Since, such particle, especially an inorganic particle, usually has a hydrophilic surface, it is difficult to be incorporated as it is into an oily base, and sometimes undergoes an aggregation. As a result, the stability of the composition becomes problematic, and a function associated naturally with a particle such as a UV scattering effect expected from a particulate titanium oxide is not exerted satisfactorily.

Accordingly, a method for increasing a lipophilicity by means of a hydrophobicity-imparting treatment of the surface of a particle, or a dispersion in which a particle was dispersed preliminarily in an oily dispersion medium together with a certain dispersant has extensively been developed. An example of the latter is a particulate titanium oxide silicone dispersion described in JP-A-9-208438, in which the particulate titanium oxide is dispersed in silicone together with a dispersant.

However, a preliminary hydrophobicity-imparting treatment of the surface of a particle, as described above, allows the treated surface to be peeled off due to the sheer force exerted when incorporating and mixing the particle with a composition such as a cosmetic formulation, resulting in a reduced dispersibility in an oily base.

A dispersion of a prior art may undergo, over a time period, a sedimentation of a particle in silicone as a dispersion medium, which is undesirable for the purpose of a consistent manufacture of a product.

On the other hand, a particle such as a particulate titanium oxide or a particulate zinc oxide may undergo, during the production method of an emulsified cosmetic product, an aggregation due to the interaction of the particle with a surfactant and water when adding the surfactant and an water phase to an oil phase containing the particle to effect an emulsification. As a result, the stability of a composition becomes problematic and a function associated naturally with a particle such as a UV scattering effect expected from a particulate titanium oxide is not exerted satisfactorily.

Lipstick

A lipstick is produced usually by a method in which a colorant powder is mixed with an oily agent using a roll mill or equivalent and then a paste composition containing a primary particle is added to a melted mixture of a solidifying agent and other oils, and the mixture is agitated using a disper or equivalent, filled and molded.

However, when a lipstick is produced by a method described above, the production cost and the production time become problematic since a preliminary roll milling process is required. A roll milling process requires a well-trained skill and involves a difficulty in being applied to a mass production. In addition, a colorant powder to be incorporated is difficult to be ground or dispersed, resulting in a functional problem, which leads to a demand of a new dispersing device.

Also because of an insufficiently ground or dispersed colorant powder to be incorporated, a resultant lipstick undergoes a problematically insufficient color development or exhibits a poor color tone, or has an insufficient gloss or extending ability, and, especially in the case of a solid lipstick, tends to be broken readily.

On the other hand, a media mill came into use recently instead of a roll mill for dispersing a pigment in the field of a paint or ink. A media mill is more excellent in grinding or dispersing a particle when compared with a roll mill, and can be used for a mass production. Also for the purpose of incorporating a particle, an oil dispersion of a titanium oxide or a colorant powder began to be produced recently. A media mill came into use as a means for dispersing a colorant powder in the production of a dispersion. An ordinary media mill has a structure in which a bead is employed as a solid dispersion medium and a colorant powder and a solvent are mixed preliminarily and then pumped to a tank in which the beads are contained and a stirring disk is rotated, where the colorant powder is ground and dispersed by the sheer force of the stirring disk and the impact of the beads. In the field of cosmetic products, a media-mill is applied to a method for producing a composite particle (JP-A-9-143030) and a method for producing a surface-treated particle (JP-A-7-108156), any of which employs a media-agitating mill called a continuous sand mill and uses only two or less of colorant powders. Such a method, when applied as it is to the production of a lipstick, requires a preliminary mixer separately in addition to a dispersing device, exerts a similarly strong mechanical force for dispersing which is not suitable to the production of a lipstick to which various types of the colorant particles are incorporated, and also employs a preliminary agitating device and a circulation pipe in addition to a dispersing device which leads to a difficulty in washing, thus presenting problematic characteristics.

The present invention is established based on the problems discussed above. The first objective of the invention is to provide a method for producing cosmetic products capable of improving a touch of the cosmetic product and also capable of fully exerting the function of powder incorporated.

The second objective of the invention is to provide a method for producing solid powdery cosmetic products which is excellent in terms of the practical performance and the impact resistance.

The third objective of the invention is to provide a method for producing powdery cosmetic products which is excellent in terms of the skin feel, the long-lasting performance of the makeup and the economical performance, and which can be used with water.

The fourth objective of the invention is to provide a method for producing an oily cosmetic product and an emulsified cosmetic product which can be used quickly, handled readily and obtained at a low cost and which allows a function of powder incorporated to be exerted sufficiently.

The fifth objective of the invention is to provide a method for producing cosmetic products using a hydrophobicity-imparted powder dispersion capable of improving the stability of the cosmetic product.

The sixth objective of the invention is to provide a method for producing an emulsified cosmetic product involving a hydrophobicity-imparting process, said cosmetic product having a high stability and a high particle dispersibility.

The seventh objective of the invention is to provide a time-saving, readily operable and economically efficient method for producing a lipstick which is excellent in the color development, the extending ability and the gloss, and, especially in the case of a solid lipstick, a lipstick which is hardly broken.

SUMMARY OF THE INVENTION

Now the inventors discovered that by applying a media-agitating mill to the production of cosmetic products containing powder the function of the powder can be improved and various characteristics of a resulting cosmetic product can be improved. The inventors also discovered that, by utilizing a media-agitating mill, an excellent dispersibility can be achieved even with particulate powder and a hydrophobicity-imparted powder. The inventors further discovered that an efficient production of cosmetic products involving a process for imparting powder with a hydrophobicity is possible using a media-agitating mill. Each cosmetic product is detailed below.

Powdery Cosmetic Product

In any conventional method for producing solid powdery cosmetic products, the mixing of powder components and oil components as binders or a surfactant is performed using an agitating mixer. The inventors considered that such mixing using an agitating mixer is not satisfactory in terms of the dispersing or grinding performance or the agitating or mixing performance and allows the aggregated particle of the powder to be deposited with the oil components only unevenly, and that because of such state a substantial improvement in the practical performance or the impact resistance is prevented partly, and finally discovered that a uniformity of the oil components in the powder components in the mixing process described above leads to the substantial improvement in the practical performance or the impact resistance.

The inventors also discovered unexpectedly, when the inventors disperse and mix an organic silicon-based resin compound, which is incorporated mainly into a liquid cosmetic product such as a liquid foundation whereby utilizing its film forming ability for the purpose of improving the long-lasting performance of the makeup and preventing a secondary deposition, and powder components in a solvent in which the organic silicon-based resin compound is soluble using a media-agitating mill, that the organic silicon-based resin compound is adsorbed onto the surface of the particle whereby imparting the surface of the powder with hydrophobicity successfully.

Accordingly, the inventors discovered that powdery cosmetic products obtained by introducing a process for imparting the surface of a particle with hydropobicity using an organic silicon-based resin compound described above, when subjected to a method for producing powdery cosmetic products comprising at least a step for mixing powder components and oil components as binders in a solvent using a media-agitating mill to form a slurry, not only exhibits a long-lasting performance of a makeup against sweat or sebum and can be used with water, but also exhibits a unique slippery skin feel and is advantageous economically compared with a conventional two-way powdered cosmetic product employing a particle whose surface has already been imparted with hydrophobicity, thus establishing the present invention.

Oily Cosmetic Product and Emulsified Cosmetic Product

The inventors discovered a method for producing cosmetic products containing particulate powder using a single media-agitating mill fitted with an in-tank stirring device in a single tank without conducting a preliminary treatment step. According to this method, since a stirring is effected by an in-tank stirring device and a solid dispersion medium is further employed for dispersing powder containing particulate powder, the powder can be finely dispersed when compared with a conventional dispersing device such as a roll mill, an atomizer, a disper and a homogenizer. As a result, it was discovered that, in the field of an oily cosmetic product, a foundation which is smooth and exhibits no dusty skin feel and which is also transparent and highly UV-protective whereby exerting a function of powder containing particulate powder sufficiently can be provided. It was also discovered that, in the field of an emulsified cosmetic product, an emulsified cosmetic product by which a function of powder containing particulate powder such as a high UV-protecting effect and a smooth texture can fully be exerted can be provided and a characteristic touch experienced as a smoothness combined with a creamy texture is attributable to an excellent emulsion stability and a fine emulsion particle as a result of an emulsification step using a solid dispersion medium.

Furthermore, it is also discovered that it is possible, by using a media-agitating mill, to perform a step for dispersing particle which is not made hydrophobic and a particle coating agent into an oily phase to impart a hydrophobicity followed by a step for adding an emulsifier and an water phase to effect an emulsification continuously in a single device, whereby obtaining an emulsified cosmetic product which is highly stable and whose particle is dispersed sufficiently.

Moreover, it is also discovered that by applying a media-agitating mill to a system containing an organically-denatured clay mineral, powder which is not made hydrophobic and a coating thereof an extremely stable hydrophobicity-imparted particle dispersion can be obtained. It is also discovered that by using such dispersion cosmetic products containing a hydrophobicity-imparted particle can readily be manufactured.

Lipstick

The inventors discovered a method for producing a lipstick using a single media-agitating mill fitted with an in-tank stirring device in a single tank without conducting a preliminary treatment step. According to this method, since a stirring is effected by an in-tank stirring device and a solid dispersion medium is further employed for dispersing a colorant powder, the colorant powder can be finely dispersed when compared with a conventional dispersing device such as a roll mill, a pulverizer, a disper and a homogenizer, whereby providing a lipstick exhibiting excellent color development, extending ability and gloss. It is also discovered that in the case of a solid lipstick one which is difficult to be broken can be provided, thus establishing the present invention.

Based on the findings described above, the inventors established the invention.

Thus, a method for producing cosmetic products is characterized by a step for dispersing powder components and oil components or aqueous components using a media-agitating mill.

In another method for producing cosmetic products according to the invention, the production of solid powdery cosmetic products involves at least a step for mixing powder components and oil components as binders in a solvent to form a slurry and wherein said mixing is performed using a media-agitating mill whereby grinding an aggregated particle of the powder components to form a slurry in a state close to a primary particle.

In a method described above, it is preferred that the slurry is made free from the solvent and filled in a container.

In a method described above, it is preferred that the slurry is made free from the solvent and filled in a container and then subjected to a dry press molding.

In a method described above, it is preferred that the slurry is filled in a container and then subjected to a suction press molding.

In a method described above, it is preferred that the solid powdery cosmetic product comprises 65 to 97% by weight of the powder components and 3 to 35% by weight of the oil components.

In another method for producing cosmetic products according to the invention, the production of powdery cosmetic products involves at least a step for mixing powder components and oil phase components as binders in a solvent using a media-agitating mill to form a slurry and wherein an organic silicon resin compound is incorporated when dispersing the powder components.

In a method described above, it is preferred that the powdery cosmetic product contains 60 to 97% by weight of powder components, 1 to 20% by weight of a particle coating agent and 2 to 30% by weight of oil components and wherein the powder components are capable to be made hydrophobic.

In another method for producing cosmetic products according to the invention, the powder components and the oil components or the aqueous components are dispersed by a solid dispersion medium using a batch media-agitating mill.

In a method described above, it is preferred that the powder components contain particulate powder whose mean particle size is 0.005 to 0.5 μm.

In a method described above, it is preferred that the solid dispersion medium is a bead selected from the group consisting of glass, alumina, zirconia, steel or flint stone.

In a method described above, it is preferred that the batch media-agitating mill comprises, in an identical tank, both of at least one basket part in which a solid dispersion medium is contained and which has a in-basket stirring device for stirring the content of the basket part and at least one in-tank stirring device for both of a preliminary mixing and a dispersion fluidization, wherein a mixture of powder components and oil components or aqueous components mixed preliminary by the in-tank stirring device runs into the basket part, the powder component is dispersed by the solid dispersion medium in the basket part and then runs as a dispersion out of the basket part, the dispersion is fluidized by the in-tank stirring device and a part of it returns into the basket part whereby effecting a circulation, and wherein the in-tank stirring device is provided in a position which does not interfere with the route of a fluid coming into and out of the basket part.

In a method described above, it is preferred that a side wall or a side wall and a bottom wall of said basket part are provided with a large number of small pores each consisting of a slit whose size does not allow the solid dispersion medium to run out of the basket part.

In a method described above, it is preferred that said in-tank stirring device for both of a preliminary mixing and a dispersion fluidization employs a disper or a homogenizer having a turbinal blade on the tip of a rotating rod or a combination thereof.

In another method for producing cosmetic products according to the invention, the production of an oily cosmetic product involves a use of a batch media-agitating mill for dispersing the powder components into the oil components.

In a method described above, it is preferred that the production of a solid oily cosmetic product involves a use of a batch media-agitating mill for dispersing the powder components into the oil components followed by an addition of a solidifying aid and the like followed by a stirring with heating followed by a compaction molding.

In another method for producing cosmetic products according to the invention, the production of an emulsified cosmetic product involves a use of a batch media-agitating mill for dispersing the powder components and the oil components or the aqueous components into the solid dispersion medium followed by an addition of the aqueous components or the oil components followed by an emulsification using a media-agitating mill.

Still another method for producing cosmetic products according to the invention comprises a step for mixing an organically-denatured clay mineral, a surfactant, a hydrophobic dispersion medium capable of dispersing and swelling said organically-denatured clay mineral in the presence of a surfactant, a particle which is not made hydrophobic and a particle coating agent to disperse said powder components into a state of a primary particle or close to a primary particle using a media-agitating mill while imparting the surface of said particle with a hydrophobicity.

Still another method for producing cosmetic products according to the invention comprises a step for mixing an organically-denatured clay mineral, a surfactant and a hydrophobic dispersion medium to form an organically-denatured clay mineral dispersion, adding a particle which is not made hydrophobic and a particle coating agent to said organically-denatured clay mineral dispersion and mixing using a media-agitating mill to impart the surface of said particle with a hydrophobicity.

In a method described above, it is preferred that the concentration of the organically-denatured clay mineral when mixing using a media-agitating mill ranges from 0.1 to 5% by weight.

In a method described above, it is preferred that the concentration of the particle which is not made hydrophobic when mixing using a media-agitating mill ranges from 5 to 50% by weight.

In a method described above, it is preferred that the particle which is not made hydrophobic is a UV-protecting particle.

In a method described above, it is preferred that the UV-protecting particle is one or more selected from the group consisting of zinc oxide, iron oxide, cerium oxide and titanates.

In a method described above, it is preferred that the particle coating agent is trimethylsiloxysilicic acid.

In another method for producing cosmetic products according to the invention, the production of an emulsified cosmetic product involves a particle hydrophobicity-imparting step for dispersing particle which is not made hydrophobic and a particle coating agent into an oily phase using a media-agitating mill to impart a hydrophobicity followed by an emulsifying step for adding an emulsifier and an water phase to effect an emulsification, both steps being conducted continuously in a single device.

In a method described above, it is preferred that the device is a batch media-agitating mill having a media mill part and a stirring device in a single tank.

In a method described above, it is preferred that the device is a continuous media-agitating mill consisting of a media mill part and a preliminary stirring tank and whose media-agitating mill is connected via a pipe with the preliminary stirring tank.

In a method described above, it is preferred that the step for an emulsification is performed using a media mill part.

In a method described above, it is preferred that the method is applied to the production of a water-in-oil emulsified cosmetic product.

In another method for producing cosmetic products according to the invention, the production of a lipstick involves a use of a batch media-agitating mill to disperse the powder components of a colorant and the oil components by a solid dispersion medium.

In a method described above, it is preferred that the production of a solid lipstick involves a use of a batch media-agitating mill to disperse the powder components of a colorant and the oil components by a solid dispersion medium followed by an addition of a solidifying aid and the like followed by a stirring with heating followed by a compaction molding.

BRIEF DESCRIPTION OF THE DRAWINGS

FIG. 1 shows an example of a batch media-agitating mill employed preferably in a method for producing cosmetic products according to the invention.

FIG. 2 shows an example of a continuous media-agitating mill employed preferably in a method for producing cosmetic products according to the invention.

DESCRIPTION OF THE PREFERRED EMBODIMENTS

The present invention relates to a production method capable of improving a function of powder contained in various cosmetic products by means of using a media-agitating mill.

A media-agitating mill according to the invention has a solid dispersion medium such as a bead contained in a container in which a stirring device for stirring the content is provided. Accordingly, when a cosmetic starting material containing a particle is placed in the container and stirred, the solid dispersion medium is also stirred together with the particle. Then the stirred solid dispersion medium can further grind and disperse an aggregated particle of the powder components. A media-agitating mill is classified to a continuous media-agitating mill and a batch media-agitating mill.

The production methods are described below on the basis of respective cosmetic products.

<Powdery Cosmetic Product>

An application of a method for producing cosmetic products according to the invention to powdery cosmetic products is detailed below.

(Solid Powdery Cosmetic Product)

A method for producing cosmetic products is characterized in that, when powder components and oil components as binders are mixed in a solvent to form a slurry, the mixing in the solvent is performed using a media-agitating mill to grind an aggregated particle of the powder components into an almost primary particle, in the state of which the slurry with the oil components is formed.

Powder Components

A powder component is not particularly limited and any material employed generally in cosmetic products can be employed. Concretely, such material may for example be, but not limited to, titanium oxide, zinc oxide, red iron oxide, yellow iron oxide, black iron oxide, ultramarineblue, cerium oxide, talc, mica, sericite, kaolin, silica, zinc stearate, fluorine phlogopite, synthesis talc, barium sulfate, boron nitride, bismuth oxychloride, alumina, magnesium carbonate, silicone powder, silicone elastic powder, polyurethane powder, cellulose powder, nylon powder, PMMA powder, starch and polyethylene powder. Powder whose surface is non-treated or treated with silicone, fluorine, tetoron, fatty acids, fatty acid soap lauroyllysine and the like may be employed. Only one, or two or more powders can be employed.

In a method for producing cosmetic products according to the invention, the amount of powder is preferably 65 to 97% by weight, more preferably, 80 to 93% by weight.

Oil Components

An oil component as a binder may, for example, be a naturally-occurring plant oil such as avocado oil, camellia oil, tortoise oil, macadamian nut oil, corn oil, mink oil, olive oil, rape seed oil, egg yolk oil, sesame oil, par chic oil, wheat germ oil, southern piece oil, castor oil, linseed oil, safflower oil, cotton seed oil, perilla oil, soybean oil, groundnut oil, brown real oil, mosquito net oil, rice bran oil, china wood oil, Japan wood oil, jojoba oil and germ oil; a liquid fat such as triglycerin, glycerin trioctanoate and glycerin triisopalmitate; an animal and plant liquid oil such as cocoa buffer, coconut oil, horse fat, hardened coconut oil, palm oil, beef fat, sheep fat, hardened beef fat, palm kernel oil, pig fat, cattle bone fat, Japan tallow kernel oil, hardened oil, cattle leg fat, Japan tallow and hardened castor oil; a wax such as beeswax, candy lilac wax, cotton wax, carnauba wax, bay berry wax, coccus pela West-wood wax, whale wax, montan wax, bran wax, lanolin, kapok wax, acetic acid lanolin, liquid state lanolin, sugar cane wax, lanolin fatty acid isopropyl, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether; a hydrocarbon oil such as liquid paraffin, ozokerite, squalene, 2,6,10,14-tetramethylpentadecane, paraffin, ceresin, squalene, vaseline and microcrystalline wax; a synthesis ester oil such as isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteril 12-hydroxystearate, ethylene glycol di-2-ethylhexanoate, dipenta erythrite fatty acid ester, N-alkyl glycol mono-isostearate, neopentyl glycol di-capriate, di-isostearil malate, glycerol di-2-heptyl undecanate, trimethylol propane tri-2-ethylhexanoate, trimethylol propane tri-isostearate, penta erythritol tetra-2-ethlhexanoate, glycerol tri-2-ethylhexanoate, trimethlol propane triisostearate, cetyl-2-ethylhexanoate, 2-ethyhexylpalmitate, glycerol trimyristate, glyceride tri-2-heptyl undecanate, methyl castor oil fatty acid, oleic acid oil, sedostearyl alcohol, aceto glyceride, 2-heptylundecyl palmitate, di-isobutyl adipate, 2-oethyl-dodecyl N-lauroil-L-glutamate, di-heptyundecil adipate, ethl laurate, di-2-ethylhexyl sebacate, 2-hexyldecil myristate, 2-hexyldecil palmitate, 2-hexyldecil adipate, diisopropyl sebacate, 2-ethylhexyl succinate, ethyl acetate, butyl acetate, amyl acetate, triethyl citrate; a silicone oil such as dimethylpolysiloxane, methylphenyl polysiloxane, methylhydrogen polysiloxane, decamethylpolysiloxane, dodecamethy polysiloxane and tetramethyl tetrahydrogen polysiloxane, as well as a fluorine resin and an acrylic resin. Only one, or two or more oil components can be employed.

In the invention, the amount of oil components is preferably 3 to 35% by weight, more preferably, 7 to 20% by weight. An amount of oil components less than 3% by weight leads to a difficulty in obtaining a product which is satisfactory in terms of the practical characteristics such as the skin adhesion and the moisturizing performance as well as the impact resistance. On the other hand, an amount exceeding 35% by weight leads to a difficulty in obtaining a product which is satisfactory in terms of the ability of extending over a skin and the long-lasting ability of the makeup.

Solvent

A solvent is not particularly limited and may, for example, be water, an alcohol such as methanol, ethanol and isopropyl alcohol and other solvents including benzene, toluene, THF, paraffin and silicone, which may be employed alone or in combination appropriately depending on the characteristics of the powdery and oil components employed. For example, oil components can be deposited selectively on the surface of powder utilizing a partial dissolution of oil components in a solvent.

Media-Agitating Mill

While a media-agitating mill employed in the invention may, for example, be a DINO-mill, a sand grinder mill, a ring mill, a pearl mill and a ball mill, it may be any mill provided that it serves as a dispersing machine capable of disintegrating an aggregated particle component into a state close to a primary particle and capable of depositing oil components uniformly over the surface of powder components. Among those listed above, a sand grinder mill is particularly preferred.

A bead employed in a media-agitating mill described above may, for example, be a bead made from glass, alumina, zirconia, steel or flint stone, with one made from zirconia being particularly preferred. The size of a bead employed in an ink industry is 0.3 to 2 mm in diameter. In the invention, however, a bead whose diameter is 1 to 10 mm is employed preferably, with 3 to 5 mm being more preferable. A too small diameter of a bead may allow an loading pigment such as mica and talc to be ground excessively. As a result, solid powdery cosmetic products after molding has a high hardness, exhibits a poor take onto a puff, and tends to undergo an undesirable caking. A too small diameter of a bead also leads to a difficulty in exerting a high dispersing force to a polymeric powder such as a silicone elastic powder (for example, torefill E-506C™: Toray-Dow Coning). A problematic crack on the surface upon molding is also experienced. A too large diameter of a bead is also undesirable since it may lead to a difficulty in grinding powder components sufficiently. By using a bead whose diameter is within the range specified above, an appropriate dispersing force is obtained even when all powder components including a loading pigment and a polymeric powder such as a silicone elastic powder are dispersed at once.

The dispersion and the mixing in the media is performed usually for 15 to 60 minutes.

Method for Producing Solid Powdery Cosmetic Product

In the invention, all particle components and oil components are mixed by a media-agitating mill as described above, and an aggregated particle of the powder components is ground into an almost primary particle, in the state of which the slurry is formed. In this manner, powder which is almost a primary particle can evenly be deposited with the oil components, whereby allowing solid powdery cosmetic products which is fully satisfactory in terms of the practical characteristics such as the extension and the adhesion over a skin, the moisturizing performance and the long-lasting ability of the makeup as well as the impact resistance came to be provided.

A slurry is adjusted preferably at a viscosity of 500 to 10000 mPa·s, especially 1000 to 8000 mPa·s.

After forming a slurry by mixing particle components and oil components as described above, the slurry is made free from a solvent by a standard method such as distillation and evaporation, and then filled in a container such as a metal or resin canister, whereby obtaining solid powdery cosmetic products.

Alternatively, the slurry is made free from a solvent and filled in a container such as a metal or resin canister, and then a dry press molding may be performed. The dry press molding can be performed by a standard method. A grinding step may also be included after removing a solvent from a slurry.

Alternatively, the slurry is filled in a container such as a metal or resin canister, and then subjected to a suction press molding. The suction press molding can be performed by a standard method.

Other Component

A solid powdery cosmetic product in the invention may further contain surfactants, dispersants, stabilizers, colorants, antiseptics, antioxidants, UV absorbers, perfumes and the like appropriately as long as the objectives of the invention are accomplished.

A surfactant is preferred especially as a dispersant. Such surfactant is preferably in the state of a liquid at ordinary temperature which exhibits a high dispersing effect. Those exemplified preferably are sorbitan sesquiisostearate and sorbitan monoisostearate.

Utility

A method for producing solid powdery cosmetic products of the invention is applied, for example, to a foundations, eye shadow, teak color, body powder, perfume powder, baby powder and face powders.

A method for producing solid powdery cosmetic products of the invention is further discussed with referring to Examples.

Evaluation of Practical Characteristics

20 Female panelists received the application of test formulations and evaluated the test formulations with regard to the moisturizing performance and the smoothness, the dusty skin feel, the long-lasting ability of the makeup and the uniform finish.

<Evaluation>

| | |
|---|---|
| 17 Panelists or more judged as good. | A |
| 12 to 16 Panelists judged as good. | B |
| 9 to 11 Panelists judged as good. | C |
| 5 to 8 Panelists judged as good. | D |
| 4 Panelists or less judged as good. | E |

Evaluation of Impact Resistance

A test formulation was press-molded in a resin canister and housed in a cosmetic compact container to obtain a test formulation. The test formulation in a horizontal position was dropped from the level of 30 cm down to an iron plate whose thickness was 20 mm and the number of the droppings until the test formulation was broken was evaluated as an index of the impact resistance.

EXAMPLE 1

COMPARATIVE EXAMPLE 1

Foundation

In Example 1, the powder components and the oil components in the formulation indicated in Table 1 shown below were mixed briefly in isopropyl alcohol using a disper to adjust the slurry viscosity at about 1500 mPa·s, and then dispersed and mixed using a sand grinder mill containing zirconia beads each of 5 mm in diameter. After evaporating isopropyl alcohol, the mixture was ground once using a pulverizer, filled in a container (resin canister) and subjected to a dry press molding by a known method.

On the other hand, Comparative example 1 employed an ordinary production method. Thus, the powder components and the oil components in the formulation identical to that in Example 1 were combined, mixed using a Henschel mixer, ground twice using a pulverizer, filled in a container (resin canister) and subjected to a dry press molding by a known method.

The foundations produced by the methods in Example 1 and Comparative example 1 were examined for the practical characteristics and the impact resistance described above. The results are shown in Table 1.

TABLE 1

|  | Example 1 | Comparative example 1 |
| --- | --- | --- |
| sericite | 17 | 17 |
| synthetic mica | 10 | 10 |
| talc | to 100 | to 100 |
| titanium oxide | 12 | 12 |
| red iron oxide | 0.8 | 0.8 |
| yellow iron oxide | 2 | 2 |
| black iron oxide | 0.1 | 0.1 |
| silicone elastic powder(*) | 6 | 6 |
| spheric polyethylene | 4 | 4 |
| dimethylpolysiloxane | 3 | 3 |
| liquid paraffin | 5 | 5 |
| vaseline | 5 | 5 |
| sorbitan sesqui isostearate | 1 | 1 |
| paraben | q.s. | q.s. |
| antioxidant | q.s. | q.s. |
| perfume | q.s. | q.s. |
| moisturizing performance | A | C |
| smoothness | A | B |
| dusty skin feel | A | C |
| long-lasting ability of makeup | B | C |
| uniform finish | A | B |
| impact resistance | 10 times | 4 times |

*trefill E-506 C ™: MANUFACTURED by TORAY DOW CORNING SILICONE Co. Ltd.

EXAMPLE 2

COMPARATIVE EXAMPLE 2

Foundation

In Example 2, the powder components and the oil components in the formulation indicated in Table 2 shown below were mixed briefly in isopropyl alcohol using a disper to adjust the slurry viscosity at about 150 mPa·s, and then dispersed and mixed using a sand grinder mill containing zirconia beads each of 1.0 mm in diameter. With evaporating isopropyl alcohol, the slurry viscosity was adjusted, and the mixture was filled in a container (resin canister) and subjected to a dry press molding by a known method.

On the other hand, Comparative example 2 employed an ordinary production method. Thus, the powder components and the oil components in the formulation identical to that in Example 2 were combined, mixed using a nautor mixer, ground twice using a pulverizer, filled in a container (resin canister) and subjected to a dry press molding by a known method.

The foundations produced by the methods in Example 2 and Comparative example 2 were examined for the practical characteristics and the impact resistance described above. The results are shown in Table 2.

TABLE 2

|  | Example 2 | Comparative example 2 |
| --- | --- | --- |
| silicone-treated sericite | 18 | 18 |
| silicone-treated mica | to 100 | to 100 |
| silicone-treated talc | 15 | 15 |
| silicone-treated titanium oxide | 10 | 10 |
| aluminum stearate-treated particulate titanium oxide | 6 | 6 |
| silicone-treated red iron oxide | 1.2 | 1.2 |
| silicone-treated yellow iron oxide | 2.5 | 2.5 |
| silicone-treated black iron oxide | 0.9 | 0.9 |
| polyurethane powder | 6 | 6 |
| paraben | q.s. | q.s. |
| dimethylpolysiloxane | 4 | 4 |
| methyl phenyl polysiloxane | 3 | 3 |
| octylmethoxycinnamate | 3 | 3 |
| polyether silicone | 2 | 2 |
| antioxidant | q.s. | q.s. |
| perfume | q.s. | q.s. |
| moisturizing performance | B | C |
| smoothness | A | B |
| dusty skin feel | B | D |
| long-lasting ability of makeup | A | B |
| uniform finish | A | B |
| impact resistance | 7 times | 4 times |

EXAMPLE 3

COMPARATIVE EXAMPLE 3

White Powder

In Example 3, the powder components and the oil components in the formulation indicated in Table 3 shown below were mixed briefly in ethyl alcohol using a disper to adjust the slurry viscosity at about 1500 mPa·s, and then dispersed and mixed using a sand grinder mill containing zirconia beads each of 1.5 mm in diameter. With evaporating ethyl alcohol, the slurry viscosity was adjusted, and the mixture was filled in a container (resin canister) and subjected to a dry press molding by a known method.

On the other hand, Comparative example 3 employed an ordinary production method. Thus, the powder components and the oil components in the formulation identical to that in Example 3 were combined, mixed using a Henschel mixer, ground twice using a pulverizer, filled in a container (resin canister) and subjected to a dry press molding by a known method.

The white powders produced by the methods in Example 3 and Comparative example 3 were examined for the practical characteristics and the impact resistance described above. The results are shown in Table 3.

TABLE 3

|  | Example 3 | Comparative example 3 |
|---|---|---|
| talc | to 100 | to 100 |
| mica | 25 | 25 |
| zinc oxide | 5 | 5 |
| particulate titanium oxide | 3 | 3 |
| spheric silicone powder | 8 | 8 |
| vaseline | 1 | 1 |
| squalane | 3 | 3 |
| ester oil | 1 | 1 |
| paraben | q.s. | q.s. |
| antioxidant | q.s. | q.s. |
| perfume | q.s. | q.s. |
| moisturizing performance | C | E |
| smoothness | A | B |
| dusty skin feel | B | C |
| long-lasting ability of makeup | B | C |
| uniform finish | A | B |
| impact resistance | 8 times | 5 times |

EXAMPLE 4

COMPARATIVE EXAMPLE 4

Face Powder

In Example 4, the powder components and the oil components in the formulation indicated in Table 4 shown below were mixed briefly in toluene using a disper to adjust the slurry viscosity at about 1500 mPa·s, and then dispersed and mixed using a sand grinder mill containing zirconia beads each of 3.0 mm in size. After evaporating toluene, the mixture was ground twice using a pulverizer, filled in a container (resin canister) as powder.

On the other hand, Comparative example 4 employed an ordinary production method. Thus, the powder components and the oil components in the formulation identical to that in Example 4 were combined, mixed using a Henschel mixer, ground twice using a pulverizer, filled in a container (resin canister) as powder.

The face powders produced by the methods in Example 4 and Comparative example 4 were examined for the practical characteristics and the impact resistance described above. The results are shown in Table 4.

TABLE 4

|  | Example 4 | Comparative example 4 |
|---|---|---|
| talc | to 100 | to 100 |
| synthetic mica | 30 | 30 |
| lamina zinc oxide | 6 | 6 |
| red iron oxide | 0.2 | 0.2 |
| yellow iron oxide | 0.7 | 0.7 |
| particulate titanium oxide | 1 | 1 |
| silicone elastic powder(*) | 10 | 10 |

TABLE 4-continued

|  | Example 4 | Comparative example 4 |
|---|---|---|
| dimethylpolysiloxane | 7 | 7 |
| paraben | q.s. | q.s. |
| antioxidant | q.s. | q.s. |
| perfume | q.s. | q.s. |
| moisturizing performance | B | D |
| smoothness | A | B |
| dusty skin feel | B | C |
| long-lasting ability of makeup | A | B |
| uniform finish | A | D |
| impact resistance | 7 times | 2 times |

*trefill E-506 C ™: TORAY DOW CORNING SILICONE Co. Ltd.

EXAMPLE 5

COMPARATIVE EXAMPLE 5

Powdery Foundation

In Example 5, the powder components and the oil components in the formulation indicated in Table 5 shown below were mixed briefly in toluene using a disper to adjust the slurry viscosity at about 1500 mPa·s, and then dispersed and mixed using a sand grinder mill containing zirconia beads each of 5.0 mm in size. After evaporating toluene, the mixture was ground twice using a pulverizer, filled in a container (resin canister) and subjected to a suction press molding by a known method.

On the other hand, Comparative example 5 employed an ordinary production method. Thus, the powder components and the oil components in the formulation identical to that in Example 5 were combined, mixed using a Henschel mixer, ground twice using a pulverizer, filled in a container (resin canister) and subjected to a dry press molding by a known method.

The foundations produced by the methods in Example 5 and Comparative example 5 were examined for the practical characteristics and the impact resistance described above. The results are shown in Table 5.

TABLE 5

|  | Example 5 | Comparative example 5 |
|---|---|---|
| sericite | 17 | 17 |
| mica | to 100 | to 100 |
| talc | 10 | 10 |
| titanium oxide | 12 | 12 |
| red iron oxide | 0.8 | 0.8 |
| yellow iron oxide | 2 | 2 |
| black iron oxide | 0.1 | 0.1 |
| silicone elastic powder(*) | 10 | 10 |
| spheric polyethylene | 4 | 4 |
| dimethylpolysiloxane | 3 | 3 |
| liquid paraffin | 5 | 5 |
| vaseline | 5 | 5 |
| sorbitan sesqui isostearate | 1 | 1 |
| paraben | q.s. | q.s. |
| antioxidant | q.s. | q.s. |
| perfume | q.s. | q.s. |
| moisturizing performance | A | C |
| smoothness | A | B |
| dusty skin feel | A | C |
| long-lasting ability of makeup | B | B |
| uniform finish | A | B |
| impact resistance | 8 times | 2 times |

*trefill E-506 C ™: TORAY DOW CORNING SILICONE Co. Ltd.

Based on the results described above, by using a media-agitating mill in the production of solid powdery cosmetic products, solid powdery cosmetic products which is excellent in the skin touch, the finish and the impact resistance can be obtained.

(Method for Producing Powdery Cosmetic Product Involving Hydrophobicity-Imparting Step)

The inventors also investigated a method for producing powdery cosmetic products involving a step for imparting powder components with hydrophobicity.

A method for producing powdery cosmetic products involving a step for imparting powder components with hydrophobicity in the invention is discussed below.

The invention is characterized in that, in the production of powdery cosmetic products involving at least a step for mixing powder components and oil phase components as binders in a solvent using a media-agitating mill to form a slurry, an organic silicon resin compound is incorporated when dispersing the powder components.

Powder Components

A powder component is not particularly limited and any material employed generally in cosmetic products can be employed. Concretely, such particles for cosmetic products may, for example, be an inorganic powder such as talc, kaolin, mica, silk mica (sericite), muscovite, phlogopite, synthesis mica, red mica, biotite, lithia mica, vermiculite, magnesium carbonate, calcium carbonate, aluminum silicate, barium silicate, calcium silicate, magnesium silicate, strontium silicate, metal tungstate, magnesium, silica, zeolite, barium sulfate, baked calcium sulfate (calcined gypsum), calcium phosphate, fluorinated apatite, hydroxy apatite, ceramic powder, metal soap (zinc myristate, calcium palmitate, aluminium stearate and the like) and boron nitride; an organic powder such as PMMA, silicone resin powder, silicone rubber powder, nylon powder, silk powder, wool powder and urethane powder; an inorganic white pigment such as titanium dioxide and zinc oxide; an inorganic red pigment such as iron oxide (red iron oxide) and iron titanate; an inorganic tan pigment such as $\gamma$-iron oxide; an inorganic yellow pigment such as yellow iron oxide and yellow ocher; an inorganic black pigment such as black iron oxide, carbon black and lower order titanium oxide; an inorganic purple pigment such as manganviolet and baltoviolet; an inorganic green pigment such as chromium oxide, chromium hydroxide and cobalt titanate; an inorganic blue pigment such as ultramarine and prussian blue; an inorganic pearl pigment such as titanium oxide coated mica, titanium oxide coated bismuth oxychloride, titanium oxide coated talc, coloring titanium oxide coated mica, bismuth oxychloride and scale powder; a metal powder pigment such as aluminium powder and copper powder; an organic pigment such as red No. 201, red No. 202, red No. 204, red No. 205, red No. 220, red No. 226, red No. 228, red No. 405, bitter orange color No. 203, bitter orange color No. 204, yellow No. 205, yellow No. 401 and Blue No. 404; an organic lake pigment such as zirconium lake, barium lake and aluminium lake including red No. 3, red No. 104, red No. 106, red No. 227, red No. 230, red No. 401, red No. 505, bitter orange color No. 205, yellow No. 4, yellow No. 5, yellow No. 202, yellow No. 203, green No. 3 and blue No. 1; and a naturally-occurring pigment such as chlorophyll and $\beta$-carotene. While a hydrophobicity-imparting treatment can be performed during the step in the invention, powder whose surface is made water-repellent can also be employed unless the effect of the invention is affected adversely. A water-repellency-imparting treatment may, for example, be a treatment with silicone, a higher fatty acid, a higher alcohol, a fatty ester, a metal soap, an amino acid, an alkyl phosphate, a cationic surfactant, a perfluoroalkyl phosphate, and a dextrin fatty ester.

In a method for producing powdery cosmetic products of the invention, the amount of the powder components to be added is preferably 60 to 97% by weight, more preferably 65 to 90% by weight.

Organic Silicon-Based Resin Compounds

An organic silicon-based resin compound employed in the invention may, for example, be trimethylsiloxysilicic acid, a fluorine-denaturated silicone resin and an acryl silicone copolymer, with trimethylsiloxysilicic acid being preferred.

The amount of an organic silicon-based resin compound incorporated in the invention is preferably 1 to 20% by weight, more preferably 5 to 15% by weight, particularly 3 to 10% by weight. An amount of an organic silicon-based resin compound less than 1% by weight does not allow the surface of powder to be imparted with hydrophobicity sufficiently, resulting in a difficulty in obtaining a product which is satisfactory with regard to the long-lasting ability of the makeup, the use of water and the slippery skin feel. On the other hand, an amount exceeding 30% by weight of an organic silicon-based resin compound does not give a correspondingly improved hydrophobicity, resulting in an economical disadvantage, sometimes accompanied with a sticky skin touch.

Oil Components

An oil component is not particularly limited and any material employed generally in cosmetic products can be employed. Concretely, such oil components may, for example, be a silicone oil such as dimethylpolysiloxane, cyclic dimethylpolysiloxane and methylphenyl polysiloxane, various hydrocarbon oils such as squalane, liquid paraffin, light-gravity isoparaffin, vaseline, microcrystan wax, ozokerite and ceresin; a higher fatty acid such as myristic acid, palmitic acid, stearic acid, oleic acid, iso stearic acid and behenic acid; a higher alcohol such as cetyl alcohol, stearyl alcohol, oleil alcohol and batyl alcohol; esters such as cetyl-2-ethylhexanoate, 2-ethylhexylpalmitate, 2-octyldodecilmylistate, neopentylglycol-2-ethylhexanoate, tri-octane acid glyceride, 2-octyldodecilolate, isopropyl mylistate, mylistyl mylistate, tri-isostearic acid glyceride, tri-oleic acid glyceride and tri-coconut oil fatty acid glyceride; a oil such as olive oil, avocado oil, jojoba oil, sunflower oil, safflower oil, camellia oil, shea butter, macadamian nut oil, mink oil, lanolin, lanolin acetate, liquid lanolin, castor oil; a wax such as Japan tallow; a fluorine-based oil such as perfluoropolyether and perfluorocarbon. Only one, or two or more oil components can be employed.

The amount of the oil components to be added in the invention is preferably 3 to 30% by weight, more preferably 7 to 20% by weight.

Other Components

In the invention, other components such as surfactants, dispersants, stabilizers, colorants, antiseptics, antioxidants, UV absorbers and perfumes may be incorporated appropriately as long as the objectives of the invention are accomplished.

Solvent

A solvent is not particularly limited as long as it can solubilize an organic silicon-based resin compound employed, and may, for example, be an alcohol such as methanol, ethanol and isopropyl alcohol as well as benzene, toluene and silicone, with ethanol and isopropyl alcohol being preferred practically.

Media-Agitating Mill

A media mill employed in the invention may for example be a media-agitating mill such as a sand grinder mill, a ring mill, a pearl mill and a ball mill, and, as a dispersing machine, it may be any mill provided that it is capable of disintegrating an aggregated particle component into a state close to a primary particle and capable of depositing oil components uniformly over the surface of powder components. Among those listed above, a media-agitating mill such as a sand grinder mill which has a relatively stronger dispersing force is particularly preferred.

Utility

A method for producing powdery cosmetic products of the invention is applied, for example, to foundations, eye shadows, cheek colors, body powders, perfume powders, baby powders and face powders.

The invention is further discussed in Examples, which are not intended to restrict the technical scope of the invention, and in which a blending quantity is shown % by weight unless otherwise specified.

Evaluation of Practical Characteristics

20 Female panelists received the application of a test formulation and evaluated the formulation with regard to the long-lasting ability of the makeup and the slippery skin feel.

<Evaluation>

| | |
|---|---|
| 17 Panelists or more judged as good. | A |
| 12 to 16 Panelists judged as good. | B |
| 9 to 11 Panelists judged as good. | C |
| 5 to 8 Panelists judged as good. | D |
| 4 Panelists or less judged as good. | E |

Hydrophobicity Test

Powder component and organic silicon-based resin compound during the production method of a product were dispersed and mixed in a solvent; and a part of the resultant slurry was taken, filtered, washed with ethanol and dried. The resultant powder was mounted on the surface of water contained in a beaker, stirred, and its hydrophobicity was determined based on whether it was dispersed in water or not.

Water Use Test

To determine whether the use of water is possible or not, a sponge for a powdery foundation retaining soaked with a suitable amount of water was used to take a suitable amount of a sample, and the sample was applied to a skin.

Experiment 1 and 2, Foundation

In Experiment 1, the powder components and the organic silicon-based resin compound in the formulation indicated in Table 6 shown below were dispersed and mixed for 15 minutes in ethanol as a solvent using a sand grinder mill containing zirconia beads, and the remainder of the oil components was added and the mixture was further dispersed and mixed for 15 minutes using the sand grinder mill to obtain a slurry, which was filled in a container (resin canister) and subjected to a suction press molding by a known method.

On the other hand, Experiment 2 employed the production method similar to Experiment 1 except for using no organic silicon-based resin compound.

TABLE 6

| | Experiment 1 | Experiment 2 |
|---|---|---|
| sericite | 10 | 10 |
| talc | to 100 | to 100 |
| mica | 15 | 15 |
| titanium oxide | 10.5 | 10.5 |
| particulate titanium oxide | 5 | 5 |
| red iron oxide | 0.8 | 0.8 |
| yellow iron oxide | 2 | 2 |
| black iron oxide | 0.1 | 0.1 |
| silicone resin spheric powder | 6 | 6 |
| trimethyl siloxysilicic acid | 10 | 10 |
| liquid paraffin | 4 | 4 |
| vaseline | 4 | 4 |
| sorbitan sesqui isostearate | 0.8 | 0.8 |
| paraben | q.s. | q.s. |
| antioxidant | q.s. | q.s. |
| perfume | q.s. | q.s. |
| long-lasting ability of makeup | A | B |
| slippery skin feel | B | D |
| hydrophobic test | no problem | dispersion |
| water use test | no problem | not usable (caking) |

As evident from Table 6, Experiment 1 in which the organic silicon-based resin compound was incorporated during the dispersion using the media-agitating mill was excellent in the long-lasting ability of the makeup and the slippery skin feel. It was also evident that Experiment 1 possessed problems in the hydrophobic test and the water use test.

On the other hand, Experiment 2 contained no organic silicon-based resin compound had a poor slipperiness, and was problematic in the hydrophobicity test and the water use test.

Experiments 3 to 5 Foundation

In Experiments 3 to 5, the formulations shown in Table 7 were used in the method similar to Experiment 1 to obtain foundations.

TABLE 7

| | Experiment 3 | Experiment 4 | Experiment 5 |
|---|---|---|---|
| sericite | 20 | 20 | 20 |
| talc | to 100 | to 100 | to 100 |
| mica | 10 | 10 | 10 |
| titanium oxide | 10.5 | 10.5 | 10.5 |
| red iron oxide | 0.8 | 0.8 | 0.8 |
| yellow iron oxide | 2 | 2 | 2 |
| black iron oxide | 0.1 | 0.1 | 0.1 |
| silicone elastic powder(*) | 6 | 6 | 6 |
| trimethyl siloxysilicic acid | 1 | 1 | 1 |
| liquid paraffin | 4 | 4 | 4 |
| vaseline | 4 | 4 | 4 |
| sorbitan sesqui isostearate | 0.8 | 0.8 | 0.8 |
| paraben | q.s. | q.s. | q.s. |
| antioxidant | q.s. | q.s. | q.s. |
| perfume | q.s. | q.s. | q.s. |
| long-lasting ability of makeup | B | A | A |
| slippery skin feel | B | A | A |
| hydrophobic test | no problem | no problem | no problem |
| water use test | no problem | no problem | no problem |

*trefill 506 C ™: TORAY DOW CORNING SILICONE Co. Ltd.

As evident from Table 7, any of Experiments 3, 4 and 5 possessed no problems with regard to the long-lasting ability of the makeup, the slippery skin feel and the results of the hydrophobicity test and the water use test. When comparing Experiment 4 and Experiment 5, there was no substantial difference in the performance. However, Experiment 5 was considered to be far less cost efficient since it used a relatively expensive organic silicon-based resin compound.

EXAMPLE 6

Face Powder

In Example 6, the powder components and the organic silicon-based resin compound in the formulation indicated in Table 8 shown below were dispersed and mixed for 15 minutes in ethanol as a solvent using a homomixer at 9000 rpm, and the remainder of the oil components was added and the mixture was further dispersed and mixed for 15 minutes using the sand grinder mill to obtain a slurry, which was evaporated to dryness to obtain powder, which was ground using a pulverizer and filled in a container as powder.

TABLE 8

|  | Experiment 6 |
| --- | --- |
| mica | 10 |
| talc | to 100 |
| zinc oxide | 5 |
| particulate titanium oxide | 3 |
| silicone spheric powder | 8 |
| trimethyl siloxysilicic acid | 10 |
| vaseline | 1 |
| squalane | 2 |
| ester oil | 1 |
| paraben | q.s. |
| antioxidant | q.s. |
| perfume | q.s. |
| long-lasting ability of makeup | A |
| slippery skin feel | A |
| hydrophobic test | no problem |

EXAMPLE 7

Face Powder

In Example 7, the powder components and the organic silicon-based resin compound in the formulation indicated in Table 9 shown below were dispersed and mixed for 15 minutes in ethanol as a solvent using a homomixer at 9000 rpm, and the remainder of the oil components was added and the mixture was further dispersed and mixed for 15 minutes using the sand grinder mill to obtain a slurry, which was evaporated to dryness to obtain powder, which was ground using a pulverizer and filled in a container as powder.

TABLE 9

|  | Experiment 7 |
| --- | --- |
| talc | to 100 |
| synthetic mica | 30 |
| red iron oxide | 0.2 |
| yellow iron oxide | 0.7 |
| particulate titanium oxide | 1 |
| silicone resin spheric powder | 10 |
| trimethyl siloxysilicic acid | 10 |
| dimethylpolysiloxane | 7 |
| paraben | q.s. |
| antioxidant | q.s. |

TABLE 9-continued

|  | Experiment 7 |
| --- | --- |
| perfume | q.s. |
| long-lasting ability of makeup | A |
| slippery skin feel | A |
| hydrophobic test | no problem |

<Method for Producing Oily Cosmetic Product and Emulsified Cosmetic Product>

The inventors also investigated a method for producing an oily cosmetic product and an emulsified cosmetic product. Such cosmetic product frequently contains particulate powder. Accordingly, the production of cosmetic products requires a strong dispersing force. It was discovered that, when producing such cosmetic product the use of a batch media-agitating mill was particularly efficient. A method for producing an oily cosmetic products and an emulsified cosmetic product is detailed below.

Batch Media-Agitating Mill

A batch media-agitating mill in the invention has a stirring device for a preliminary stirring and a media mill part which are provided separately but in an identical tank. The media mill part has solid dispersion media such as beads contained in a container in which a stirring device for stirring the content is provided. In the inside of the media mill part and the inside of the tank, a fluid containing a particle is allowed to travel. Accordingly, when a cosmetic starting material containing a particle is placed in the tank, it is agitated by the stirring device for the preliminary stirring. Subsequently, when the media mill part is actuated to agitate the content of the media mill part, the solid dispersion media is also agitated together with the particle. Then the stirred solid dispersion media can further grind and disperse an aggregated particle of the powder components. When using such batch media-agitating mill, the stirring device for the preliminary mixing and the media mill part can repetitively be actuated any times as desired. The fluid containing the particle can also be circulated in the media mill part and the tank. As a result, the batch media-agitating mill allows cosmetic products to be produced in a single tank.

An embodiment of a batch media-agitating mill which is a dispersing device employed in a production method of the invention is shown in FIG. 1(A).

As shown in FIG. 1(A), a batch media-agitating mill employed in a production method of the invention is provided with basket part 10 in tank 18, in association with at least one in-tank stirring device 20 for both of a preliminary mixing and a dispersion fluidization. Basket part 10 is provided with jacket 28 as an upper lid, and positioned by rod 16. On the side wall of basket part 10, a large number of small pores each consisting of a slit are provided. Basket part 10 is provided also with in-basket stirring device 14 for agitating the content of basket part 10.

Powder containing particulate powder that is cosmetic starting material and oil component or aqueous component are first mixed preliminarily by in-tank stirring device 20 to form a fluid mixture, which is then introduced into basket part 10 via an opening surrounding the rotation spindle of in-basket stirring device 14 fixed on the machine at the top of basket part 10.

The inner view of basket part 10 is shown in FIG. 1(B). Solid dispersing media (beads) 22 are contained in basket part 10, and in-basket stirring device 14 is provided with stirring pin disk 26 (or stirring disk) mounted vertically to the rotation spindle. Stirring pin disk 26 is provided with pin 24 for stirring.

The fluid mixture introduced into basket part 10 is brought into contact with a stirring pin disk 26 which rotates at a high speed and pulverizes and disperses an aggregated particle of the powder components in cooperation with solid dispersing media (beads) 22 and then allowed to flow out via a large number of small pores 12 each consisting of slits provided on the side wall of basket part 10.

An arrow mark of FIG. 1(A) shows an overall fluid route.

The dispersion thus allowed to flow out is then dispersed and fluidized by in-tank stirring device 20 and a part of it returns into basket part 10 via the opening at the top of basket part 10 to circulate through tank 18. It should be noted that the stirring part of in-tank stirring device 20 is located at a place which does not interfere the route of a flow into and out of basket part 10. A batch media-agitating mill is a machine having a step capable of keeping a uniform dispersion of powder in tank 18 as described above. An example of such dispersing machine employed preferably in the invention is one disclosed in JP-B-8-17930.

A basket part filled with solid dispersing media (beads) which is provided in a batch media-agitating mill described above possesses on its side wall a large number of small pores each consisting of slits of a size which does not allow the solid dispersing media (beads) to go out of the basket part, whereby preventing any the solid dispersing media from being contained in the cosmetics products which are obtained.

A batch media-agitating mill employed preferably in the invention is provided with small pores on the side wall of the basket part filled with the solid dispersing media. Accordingly, the rotation of a spindle exerts a centrifugal force, which localizes the solid dispersing media on the side wall, and powder containing particulate powder passes through a zone where the solid dispersing media exist at a high density, whereby the dispersion efficiency can be raised.

A solid dispersion medium in the invention may be a bead made from glass, alumina, zirconia, steel or flint stone, with one made from zirconia being particularly preferred. The size of a bead is generally 0.3 to 2 mm in diameter, with one whose size is about 1 mm being preferred in the invention.

As an in-tank stirring device for both of a preliminary mixing and a dispersion fluidization, a stirring device employed ordinarily in the production of a cosmetic may be employed, with a disper having a turbinal blade on the tip of a rotating rod being employed preferably.

A method for producing an oily cosmetic product and an emulsified cosmetic product is exemplified in detail below.

Method for Producing Oily Cosmetic Product

In an example of a method for producing an oily cosmetic product, a batch media-agitating mill having an in-tank stirring device is used to mix oil components and powders by the in-tank stirring device and then a basket part as a media mill part is used to disperse and mix the formulation, which is then supplemented if necessary with a wax and melted by heating, and then filled into a certain mold to obtain an oily cosmetic product. As a result, an oily cosmetic product containing various types of powders can be produced in a single tank within a short time at a low cost. A washing step after the production can also be simplified substantially when compared with a conventional method. Moreover, an oily cosmetic product obtained according to the invention in which powder containing particulate powder has been ground and dispersed excellently provides an oily foundation which gives a smooth and light texture and a clear finish as well as a high UV-protecting effect.

Method for Producing Emulsified Cosmetic Product

In an example of a method for producing an emulsified cosmetic product, a batch media-agitating mill having an in-tank stirring device is used, in the case of a water-in-oil emulsified cosmetic product, to mix oil components and powders by the in-tank stirring device and then a basket part as a media mill part is used to disperse and mix the formulation, which is then supplemented with aqueous component to form a dispersion which is stirred in the tank by a mixing stirring device while effecting an emulsification by means of the media mill part to obtain the water-in-oil emulsified cosmetic product. Alternatively, the aqueous components described above are mixed with powders by an in-tank stirring device and then dispersed and mixed in a basket part as a media mill part, and then supplemented with oil components to form a dispersion which is stirred in the tank by a mixing stirring device while effecting an emulsification by means of the media mill part to obtain the oil-in-water emulsified cosmetic product. According to the method, an emulsified cosmetic product containing particulate powders can be produced in a single tank within a short time by a simple operation at a low cost. Moreover, an emulsified cosmetic product containing particulate powders obtained according to the invention exhibits a high UV-protecting effect resulted from powder containing particulate powders which has been ground and dispersed excellently as well as a smooth and creamy texture resulted from the emulsifying step using a media-agitating mill.

Particulate Powder Components

Particulate powder in the invention may, for example, be a particulate whose mean particle size is 0.005 to 0.5 µm selected from particulate titanium oxide, particulate zinc oxide, particulate red iron oxide, particulate yellow iron oxide, particulate black iron oxide, particulate cobalt blue and the like. Particulate powder obtained by treating the surface of any particulate powder described above with silicone, fluorine, Teflon, fatty acids, fatty acid soaps, lauroyllysine and the like may also be employed. Particulate powder is known to be more excellent in the UV-protecting effect and the transparency when compared with an ordinary powder. One or more such powders are present preferably in an amount of 1 to 20% by weight in 1 to 60% by weight of the powder components. An amount less than 1% by weight may lead to a difficulty in exerting the effect of particulate powder, while an amount exceeding 20% by weight presents a large specific surface area of the powder which leads to a poor wettability in oil components, resulting in a dusty skin feel and a poor moldability.

In the invention, powder larger than particulate powder, i.e., powder having a particle size which is ordinary in cosmetic products, i.e. a size larger than 0.5 µm may also be employed.

Powder Components

A powder component in the invention may, for example, be an inorganic powder such as titanium oxide, zinc oxide, red iron oxide, yellow iron oxide, black iron oxide, ultramarineblue, cerium oxide, talc, mica, sericite, kaolin, silica, zinc stearate, fluorine phlogopite, synthesis talc, barium sulfate, magnesium carbonate and boron nitride; an organic powder component such as nylon powder, polyethylene powder, silicone powder, silicone elastic powder, polyurethane powder, cellulose powder, PMMA powder, polyethylene powder; an inorganic white pigment such as titanium oxide and zinc oxide; an inorganic colored pigment such as red iron oxide, yellow iron oxide, black iron oxide, carbon black, manganese violet, cobalt violet, ultramarineblue and prussian blue; a pearl pigment such as titanium oxide coated mica, titanium oxide coated talc, coloring titanium oxide coated mica, bismuth oxychloride and scale powder; a metal powder pigment such as alumina; an organic pigment such as zirconium, barium or aluminium lake including red No. 201, red No. 202, red No. 204, red No. 205, red No. 220, red No. 226, red No. 228, red No. 305, bitter orange No. 203, bitter orange No. 204, yellow No. 205, yellow No. 401, blue No. 404, red No. 3, red No. 104, red No. 106, red No. 227, red No. 230, red No. 401, red No. 505, bitter orange No. 205, yellow No. 4, yellow No. 5, yellow No. 202 and yellow No. 203. Powder obtained by treating the surface of any powder described above with silicone, fluorine, teflon, fatty acids, fatty acid soaps, lauroyllysine and the like may also be employed. One or more of these powders are added preferably in an amount of 1 to 60% by weight.

Oil Components

Oil components in the invention may, for example, be an ester oil such as cetyl iso-octanoate, glyceryl tri-hexanoate and isopropyl myristate; a hydrocarbon-based oil such as vaseline, liquid paraffin and squalane; a naturally occurring animal and plant oil such as castor oil, olive oil, camellia oil, jojoba oil and lanolin, which are employed in combination. The oil components are present preferably in an amount of 25 to 90% by weight in total.

Solidifying Agent

When a solid oily cosmetic product is produced in the invention, a solidifying agent preferably contains wax components. The wax components in a solidifying agent may, for example, be a combination of microcristan wax, carnauba wax, candy lilac wax, polyethylene wax and ceresin wax. The wax components are contained preferably in an amount of 3 to 25% by weight in total.

Aqueous Components

An aqueous component employed in the invention may, for example, be a polyhydric alcohol such as glycerin, a water-soluble substance such as ethyl alcohol, water and the like.

Other Components

A cosmetic product according to the invention may further contain additives such as surfactants, dispersants, stabilizers, colorants, antiseptics, antioxidants, UV absorbers, humectants and perfumes appropriately as long as the objectives of the invention are accomplished.

Utility

A method for producing cosmetic products of the invention is applied for example to an oily cosmetic product such as eye liner pencil, eye brow pencil, oily foundation, oily stick foundation, an oily eye color; an emulsified cosmetic product such as an emulsified sunscreen and emulsified foundation.

The present invention is further described in Examples, which are not intended to restrict the invention.

The invention can preferably be applied to the production of an oily cosmetic product containing 1 to 60% by weight of powder components including particulate powders, 25 to 90% by weight of oil components and 0 to 25% by weight of wax components.

The invention can preferably be applied also to the production of an emulsified cosmetic product containing 10 to 60% by weight of powder components including particulate powders, 20 to 50% by weight of oil components and 10 to 50% by weight of aqueous components.

Concrete examples are described below. The evaluation of practical characteristics were performed as detailed below.

Evaluation of Practical Characteristics

20 Female panelists received the application of a test formulation and evaluated the formulation with regard to the moisturizing performance and the smoothness, the dusty skin feel, the uniform finish and the transparency.

<Evaluation>

| | |
|---|---|
| 17 Panelists or more judged as good. | A |
| 12 to 16 Panelists judged as good. | B |
| 9 to 11 Panelists judged as good. | C |
| 5 to 8 Panelists judged as good. | D |
| 4 Panelists or less judged as good. | E |

Evaluation of SPF (UV-Controlling Effect)

A spectro radiometer method was employed to determine in vitro SPF values.

Examples of oily cosmetic products are described below.

EXAMPLE 8

COMPARATIVE EXAMPLE 6-1, 6-2

Oily Stick Foundation

Table 10 shows an oily stick foundation as Example 8 produced by a production method of the invention. The powder component and the oil components in the formulation indicated below were mixed for 10 minutes by a disper fitted in a batch media-agitating mill. Subsequently, a basket part containing zirconia beads each in 1 mm in diameter was driven to disperse and mix the formulation for 30 minutes. Wax components were added and the tank was heated to 90 to 95° C. Subsequently, the formulation was cast as melted into a stick mold, which was cooled to obtain a stick foundation. On the other hand, Comparative example 6-1 and 6-2 employed an ordinary production method. In Comparative example 6-1, the powder components in the formulation identical to that in Example 8 were ground twice using a pulverizer, added to a melted mixture of the oil components and the wax components in the tank, dispersed and mixed for 10 minutes by a homogenizer, and molded into a stick foundation by a method similar to that in Example. In Comparative example 6-2, a stick foundation was molded by a method similar to that in Comparative example 6-1 except for using an ordinary iron oxide instead of the particulate powder.

TABLE 10

| Oily stick foundation | Example 8 | Comparative example 6-1 | Comparative example 6-2 |
|---|---|---|---|
| ceresin wax | 6 | 6 | 6 |
| carnauba wax | 1 | 1 | 1 |
| dimethylpolysiloxane | 15 | 15 | 15 |
| methylphenyl polysiloxane | 15 | 15 | 15 |
| silicone resin | 2 | 2 | 2 |
| trimethylol propane tri-octate | too 100 | too 100 | too 100 |
| squalane | 10 | 10 | 10 |
| sorbitan sesqui isostearate | 2 | 2 | 2 |
| octylmethoxy cinnamate | 3 | 3 | 3 |
| sericite | 3 | 3 | 3 |

TABLE 10-continued

| Oily stick foundation | Example 8 | Comparative example 6-1 | Comparative example 6-2 |
|---|---|---|---|
| particulate titanium oxide | 15 | 15 | 15 |
| titanium oxide | 10 | 10 | 10 |
| particulate yellow iron oxide | 2.5 | 2.5 | — |
| particulate red iron oxide | 0.8 | 0.8 | — |
| particulate black iron oxide | 0.1 | 0.1 | — |
| yellow iron oxide | — | — | 2.5 |
| red iron oxide | — | — | 0.8 |
| black iron oxide | — | — | 0.1 |
| spheric silicone powder | 6 | 6 | 6 |
| antioxidant | q.s. | q.s. | q.s. |
| perfume | q.s. | q.s. | q.s. |
| smoothness | A | C | B |
| dusty skin feel | B | C | C |
| uniform finish | A | B | C |
| transparency | A | B | C |
| SPF | 44 | 36 | 34 |

As evident from the results shown in Table 10, the stick foundation (Example 8) obtained by a production method employing a batch media-agitating mill according to the invention was excellent in the skin touch, the finish, the transparency and the UV-protecting effect (SPF value) because of satisfactorily dispersed particulate powders such as particulate yellow iron oxide, particulate red iron oxide, particulate black iron oxide and other powders. On the contrary, the stick foundations (Comparative example 6-1 and 6-2) produced only by an ordinary dispersing device such as a homogenizer were poor in terms of the skin touch, the finish, the transparency and the UV-protecting effect (SPF value) when compared with the inventive stick foundation because of insufficiently dispersed particulate powders described above. While particulate powder is known to be more effective than ordinary powders, no substantial improvement of Comparative example 6-1 over Comparative example 6-2 indicates that a stick foundation produced by an ordinary method can not fully exert the effect of the particulate powder.

EXAMPLE 9

COMPARATIVE EXAMPLE 7-1, 7-2

Oily Foundation

Table 11 shows an oily foundation as Example 9 produced by a production method of the invention. The powder components and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes to obtain an oily foundation. On the other hand, Comparative example 7-1 and 7-2 employed an ordinary production method. In Comparative example 7-1, the powder components in the formulation identical to that in Example 9 were ground twice using a pulverizer, added to the oil components, dispersed and mixed for 10 minutes by a homogenizer to obtain an oily foundation. In Comparative example 7-2, an oily foundation was obtained by a method similar to that in Comparative example 7-1 except for using an ordinary iron oxide instead of the particulate powder.

[Table 11]

| Oily foundation | Example 9 | Comparative example 7-1 | Comparative example 7-2 |
|---|---|---|---|
| volatile silicone | too 100 | to 100 | to 100 |
| silicone resin | 8 | 8 | 8 |
| polyoxyethylene.methylpolysiloxane copolymer | 1 | 1 | 1 |
| alcohol | 8 | 8 | 8 |
| octylmethoxy cinnamate | 7 | 7 | 7 |
| silicone-treated talc | 14 | 14 | 14 |
| silicone-treated titanium oxide | 6 | 6 | 6 |
| stearic aluminium-treated particulate titanium oxide | 15 | 15 | 15 |
| silicone-treated particulate red iron oxide | 0.3 | 0.3 | — |
| silicone-treated particulate yellow iron oxide | 2 | 2 | — |
| silicone-treated particulate black iron oxide | 0.2 | 0.2 | — |
| silicone-treated red iron oxide | — | — | 0.3 |
| silicone-treated yellow iron oxide | — | — | 2 |
| silicone-treated black iron oxide | — | — | 0.2 |
| silicone elastic powder | 2.5 | 2.5 | 2.5 |
| antioxidant | q.s. | q.s. | q.s. |
| perfume | q.s. | q.s. | q.s. |
| moisturizing performance | B | C | C |
| smoothness | A | B | B |
| dusty skin feel | B | C | C |
| uniform finish | A | C | B |
| transparency | A | B | C |
| SPF | 53 | 45 | 42 |

As evident from the results shown in Table 11, the oily foundation (Example 9) obtained by a production method employing a batch media-agitating mill according to the invention was excellent in the skin touch, the finish, the transparency and the UV-protecting effect (SPF value) because of satisfactorily dispersed particulate powders such as particulate yellow iron oxide, particulate red iron oxide, particulate black iron oxide and other powders. On the contrary, the oily foundations (Comparative example 7-1 and 7-2) produced only by an ordinary dispersing device such as a homogenizer were poor in terms of the skin touch, the finish, the transparency and the UV-protecting effect (SPF value) when compared with the inventive oily foundation because of insufficiently dispersed particulate powders described above. While particulate powder is known to be more effective than ordinary powders, no substantial improvement of Comparative example 7-1 over Comparative example 7-2 indicates that an oily foundation produced by an ordinary method can not fully exert the effect of the particulate powder.

EXAMPLE 10

COMPARATIVE EXAMPLE 8

Oily Stick Foundation

Table 12 shows an oily stick foundation as Example 10 produced by a production method of the invention. The powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes. Wax components were added and the tank was heated to 90 to 95° C., and then the formulation was cast as melted into a stick mold, which was cooled to obtain a stick foundation. On the other hand, Comparative example 8 employed an ordinary production method. The powder components in the formulation identical to that in Example 10 were ground twice using a pulverizer, added to a melted mixture of the oil components and the wax components in the tank, dispersed and mixed for 10 minutes by a homogenizer, and molded into a stick foundation by a method similar to that in Example 10.

TABLE 12

| Oily stick foundation | Example 10 | Comparative example 8 |
|---|---|---|
| ceresin wax | 6 | 6 |
| carnauba wax | 1 | 1 |
| dimethylpolysiloxane | 15 | 15 |
| methylphenyl polysiloxane | 15 | 15 |
| silicone resin | 2 | 2 |
| trimethylol pronane trioctanate | to 100 | to 100 |
| squalane | 10 | 10 |
| sorbitan sesqui isostearate | 2 | 2 |
| octylmethoxy cinnamate | 3 | 3 |
| sericite | 3 | 3 |
| particulate titanium oxide | 20 | 20 |
| titanium oxide | 10 | 10 |
| yellow iron oxide | 2.5 | 2.5 |
| red iron oxide | 0.8 | 0.8 |
| black iron oxide | 0.1 | 0.1 |
| spheric silicone powder | 6 | 6 |
| antioxidant | q.s. | q.s. |
| perfume | q.s. | q.s. |
| smoothness | A | B |
| dusty skin feel | B | C |
| uniform finish | A | B |
| SPF | 48 | 38 |

As evident from the results shown in Table 12, the oily stick foundation (Example 10) obtained by a production method employing a batch media-agitating mill according to the invention was excellent in the skin touch, the uniform finish and the UV-protecting effect (SPF value) because of a satisfactorily dispersed particulate powder which was particulate titanium oxide and other powders. On the contrary, the oily stick foundation (Comparative example 8) produced only by an ordinary dispersing device such as a homogenizer was poor in terms of the skin touch, the uniform finish and the UV-protecting effect (SPF value) when compared with the inventive oily stick foundation because of insufficiently dispersed powders described above.

EXAMPLE 11

COMPARATIVE EXAMPLE 9

Oily Foundation

Table 13 shows an oily foundation as Example 11 produced by a production method of the invention. In Example 11, the powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes to obtain an oily foundation. On the other hand, Comparative example 9 employed an ordinary production method. The powder components in the formulation identical to that in Example 11 were ground twice using a pulverizer, added to the oil components, dispersed and mixed for 10 minutes by a homogenizer to obtain an oily foundation.

TABLE 13

| Oily foundation | Example 11 | Comparative Example 9 |
|---|---|---|
| volatile silicone | to 100 | to 100 |
| silicone resin | 8 | 8 |
| polyoxyethylene-methylpolysiloxane copolymer1 | 1 | 1 |
| alcohol | 8 | 8 |
| octylmethoxy cinnamate | 7 | 7 |
| silicone-treated talc | 14 | 14 |
| silicone-treated titanium oxide | 6 | 6 |
| stearic aluminium-treated particulate titanium oxide | 15 | 15 |
| silicone-treated particulate red iron oxide | 0.3 | 0.3 |
| silicone-treated particulate yellow iron oxide | 2 | 2 |
| silicone-treated particulate black iron oxide | 0.2 | 0.2 |
| silicone elastic powder | 2.5 | 2.5 |
| antioxidant | q.s. | q.s. |
| perfume | q.s. | q.s. |
| moisturizing performance | B | C |
| smoothness | A | B |
| dusty skin feel | B | C |
| uniform finish | A | C |
| SPF | 50 | 43 |

As evident from the results shown in Table 13, the oily foundation (Example 11) obtained by a production method employing a batch media-agitating mill according to the invention was excellent in the skin touch, the uniform finish and the UV-protecting effect (SPF value) because of a satisfactorily dispersed particulate powder which was aluminium stearate-treated particulate titanium oxide and other powders. On the contrary, the oily foundation (Comparative example 9) produced only by an ordinary dispersing device such as a homogenizer was poor in terms of the skin touch and the uniform finish, the UV-protecting effect (SPF value) when compared with the inventive oily foundation because of insufficiently dispersed powders described above.

Examples of emulsified cosmetic products are described below.

EXAMPLE 12

COMPARATIVE EXAMPLE 10

Water-in-Oil Emulsified Sunscreen

Table 14 shows a water-in-oil sunscreen as Example 12 produced by a production method of the invention. In Example 12, the powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes. Then aqueous components were added and the formulation in the tank was mixed by the disper while emulsifying by the media-agitating mill to obtain a sunscreen. On the other hand, Comparative example 10 employed an ordinary production method. The powder components in the formulation identical to that in Example 12 were added to the oil components, dispersed by a homogenizer for 10 minutes, combined with the aqueous components and emulsified by the homogenizer to obtain a sunscreen.

TABLE 14

| water-in-oil emulsified sunscreen | Example 12 | Comparative Example 10 |
|---|---|---|
| volatile silicone | to 100 | to 100 |
| dimethylpolysiloxane | 5 | 5 |
| polyoxyethylene·methylpolysiloxane copolymer | 3 | 3 |
| organically-denaturated bentonite | 1 | 1 |
| silicone-treated talc | 10 | 10 |
| stearic aluminium-treated particulate titanium oxide | 7 | 7 |
| silicone elastic powder | 3 | 3 |
| ion-exchanged water | 35 | 35 |
| glycerin | 5 | 5 |
| antiseptic | q.s. | q.s. |
| antioxidant | q.s. | q.s. |
| perfume | q.s. | q.s. |
| moisturizing performance | B | C |
| smoothness | A | B |
| dusty skin feel | B | C |
| uniform finish | A | C |
| SPF | 33 | 24 |

As evident from the results shown in Table 14, the water-in-oil emulsified sunscreen (Example 12) obtained by a production method employing a batch media-agitating mill according to the invention was excellent in the skin touch, the finish and the UV-protecting effect (SPF value) because of a satisfactorily dispersed particulate powder which was aluminium stearate-treated particulate titanium oxide and other powders. On the contrary, the water-in-oil emulsified sunscreen (Comparative example 10) produced only by an ordinary dispersing device such as a homogenizer was poor in terms of the skin touch, the finish, the transparency and the UV-protecting effect (SPF value) when compared with the inventive water-in-oil emulsified sunscreen because of insufficiently dispersed powders containing the particulate powder described above.

EXAMPLE 13

COMPARATIVE EXAMPLE 11

Water-in-Oil Emulsified Foundation

Table 15 shows a water-in-oil foundation as Example 13 produced by a production method of the invention. In Example 13, the powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes. Then aqueous components were added and the formulation in the tank was mixed by the disper while emulsifying by the media-agitating mill to obtain a foundation. On the other hand, Comparative example 11 employed an ordinary production method. Thus, in Comparative example 13, the powder components in the formulation identical to that in Example 13 were added to the oil components, dispersed by a homogenizer for 10 minutes, combined with the aqueous components and emulsified by the homogenizer to obtain a foundation.

TABLE 15

| water-in-oil emulsified foundation | Example 13 | Comparative Example 11 |
|---|---|---|
| volatile silicone | to 100 | to 100 |
| dimethylpolysiloxane | 5 | 5 |
| polyoxyethylene·methylpolysiloxane copolymer | 3 | 3 |
| organically-denaturated bentonite | 1 | 1 |
| silicone-treated titanium oxide | 6 | 6 |
| stearic aluminium-treated particulate titanium oxide | 10 | 10 |
| silicone-treated red iron oxide | 0.3 | 0.3 |
| silicone-treated yellow iron oxide | 2 | 2 |
| silicone-treated black iron oxide | 0.2 | 0.2 |
| silicone elastic powder | 5 | 5 |
| nylon powder | 5 | 5 |
| ion-exchanged water | 30 | 30 |
| humectant | 5 | 5 |
| antiseptic | q.s. | q.s. |
| antioxidant | q.s. | q.s. |
| perfume | q.s. | q.s. |
| moisturizing performance | B | C |
| smoothness | A | B |
| dusty skin feel | B | C |
| uniform finish | A | B |
| SPF | 30 | 22 |

As evident from the results shown in Table 15, the water-in-oil emulsified foundation (Example 13) obtained by a production method employing a batch media-agitating mill according to the invention was excellent in the skin touch, the finish and the UV-protecting effect (SPF value) because of a satisfactorily dispersed particulate powder which was aluminium stearate-treated particulate titanium-oxide and other powders. On the contrary, the water-in-oil emulsified foundation (Comparative example 11) produced only by an ordinary dispersing device such as a homogenizer was poor in terms of the skin touch, the finish, the uniform finish and the UV-protecting effect (SPF value) when compared with the inventive water-in-oil emulsified foundation because of insufficiently dispersed powders containing the particulate powder described above.

EXAMPLE 14

COMPARATIVE EXAMPLE 12-1, 12-2

Water-in-Oil Emulsified Foundation

Table 16 shows a water-in-oil foundation as Example 14 produced by a production method of the invention. The powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes. Then aqueous components were added and the formulation in the tank was mixed by the disper while emulsifying by the media-agitating mill to obtain a foundation. On the other hand, Comparative example 12-1 and 12-2 employed an ordinary production method. In Comparative example 12-1, the powder components in the formulation identical to that in Example 14 were added to the oil components, dispersed by a homogenizer for 10 minutes, combined with the aqueous components and emulsified by the homogenizer to obtain a foundation. In Comparative example 12-2, a foundation was obtained by a method similar to that in Comparative example 12-1 except for using an ordinary iron oxide instead of the particulate powder.

TABLE 16

|  | Example | Comparative example | |
|---|---|---|---|
| water-in-oil emulsified foundation | 14 | 12-1 | 12-2 |
| volatile silicone | to 100 | to 100 | to 100 |
| dimethylpolysiloxane | 5 | 5 | 5 |
| polyoxyethylene·methylpolysiloxane copolymer | 3 | 3 | 3 |
| organically-denatured bentonite | 1 | 1 | 1 |
| silicone-treated titanium oxide | 6 | 6 | 6 |
| stearic aluminium-treated·particulate titanium oxide | 10 | 10 | 10 |
| silicone-treated particulate red iron oxide | 0.3 | 0.3 | — |
| silicone-treated particulate yellow iron oxide | 2 | 2 | — |
| silicone-treated particulate black iron oxide | 0.2 | 0.2 | — |
| silicone-treated red iron oxide | — | — | 0.3 |
| silicone-treated yellow iron oxide | — | — | 2 |
| silicone-treated black iron oxide | — | — | 0.2 |
| silicone elastic powder | 5 | 5 | 5 |
| nylon powder | 5 | 5 | 5 |
| ion-exchanged water | 30 | 30 | 30 |
| humectant | 5 | 5 | 5 |
| antiseptic | q.s. | q.s. | q.s. |
| antioxidant | q.s. | q.s. | q.s. |
| perfume | q.s. | q.s. | q.s. |
| moisturizing performance | B | C | C |
| smoothness | A | C | B |
| dusty skin feel | B | C | C |
| uniform finish | A | C | B |
| SPF | 32 | 24 | 22 |

As evident from the results shown in Table 16, the water-in-oil emulsified foundation (Example 14) obtained by a production method employing a batch media-agitating mill according to the invention was excellent in the skin touch, the uniform finish and the UV-protecting effect (SPF value) because of satisfactorily dispersed particulate powders such as aluminium stearate-treated particulate titanium oxide, particulate red iron oxide, particulate yellow iron oxide, particulate black iron oxide and other powders. On the contrary, the water-in-oil emulsified foundations (Comparative example 12-1 and 12-2) produced only by an ordinary dispersing device such as a homogenizer were poor in terms of the skin touch and the uniform finish and the UV-protecting effect (SPF value) when compared with the inventive water-in-oil emulsified foundation because of insufficiently dispersed particulate powders described above. While particulate powder is known to be more effective than ordinary powders, no substantial improvement of Comparative example 12-1 over Comparative example 12-2 indicates that a water-in-oil foundation produced by an ordinary method can not fully exert the effect of the particulate powder.

EXAMPLE 15

COMPARATIVE EXAMPLE 13

Oil-in-Water Emulsified Sunscreen

Table 17 shows a oil-in-water sunscreen as Example 15 produced by a production method of the invention. The powder component and the aqueous components in the formulation indicated below were mixed for 10 minutes by a disper fitted in a batch media-agitating mill, and then a basket part containing zirconia beads each in 1 mm in diameter was driven to disperse and mix the formulation for 30 minutes. Then oil components were added and the formulation in the tank was mixed by the disper while emulsifying by the media-agitating mill to obtain a sunscreen. On the other hand, Comparative example 13 employed an ordinary production method. The powder components in the formulation identical to that in Example 15 were added to the aqueous components, dispersed by a homogenizer for 10 minutes, combined with the oil components and emulsified by the homogenizer to obtain a sunscreen.

TABLE 17

| oil-in-water emulsified sunscreen | Example 15 | Comparative example 13 |
|---|---|---|
| squalane | to 100 | to 100 |
| olive oil | 5 | 5 |
| octylmethoxy cinnamate | 5 | 5 |
| stearic acid | 2 | 2 |
| glyceryl monostearate | 2 | 2 |
| POE(40) sorbitan monostearate | 2 | 2 |
| talc | 8 | 8 |
| particulate titanium oxide | 7 | 7 |
| particulate zinc oxide | 10 | 10 |
| ion-exchanged water | 45 | 45 |
| glycerin | 5 | 5 |
| antiseptic | q.s. | q.s. |
| antioxidant | q.s. | q.s. |
| perfume | q.s. | q.s. |
| moisturizing performance | B | C |
| smoothness | A | B |
| dusty skin feel | B | C |
| uniform finish | A | C |
| SPF | 26 | 20 |

As evident from the results shown in Table 17, the oil-in-water emulsified sunscreen (Example 15) obtained by a production method employing a batch media-agitating mill according to the invention was excellent in the skin touch, the uniform finish and the UV-protecting effect (SPF value) because of a satisfactorily dispersed particulate powder which was aluminium stearate-treated particulate titanium oxide and other powders. On the contrary, the oil-in-water emulsified sunscreen (Comparative example 13) produced only by an ordinary dispersing device such as a homogenizer was poor in terms of the skin touch and the uniform finish and the UV-protecting effect (SPF value) when compared with the inventive oil-in-water emulsified sunscreen because of insufficiently dispersed powders containing the particulate powder described above.

EXAMPLE 16

COMPARATIVE EXAMPLE 14-1, 14-2

Oil-in-Water Emulsified Foundation

Table 18 shows a oil-in-water foundation as Example 16 produced by a production method of the invention. The powder component and the aqueous components in the formulation indicated below were mixed for 10 minutes by a disper fitted in a batch media-agitating mill, and then a basket part containing zirconia beads each in 1 mm in diameter was driven to disperse and mix the formulation for 30 minutes. Then oil components were added and the formulation in the tank was mixed by the disper while emulsifying by the media-agitating mill to obtain a foundation. On the other hand, Comparative example 14-1 and 14-2 employed an ordinary production method. In Comparative example 14-1, the powder components in the formulation identical to that in Example 16 were added to the aqueous components, dispersed by a homogenizer for 10 minutes, combined with the oil components and emulsified by the homogenizer to obtain a foundation. In Comparative example 14-2, a foundation was obtained by a method similar to that in Comparative example 14-1 except for using an ordinary iron oxide instead of the particulate powder.

TABLE 18

| oil-in-water emulsified foundation | Example | Comparative example | |
|---|---|---|---|
| | 16 | 14-1 | 14-2 |
| squalane | to 100 | to 100 | to 100 |
| olive oil | 10 | 10 | 10 |
| stearic acid | 2 | 2 | 2 |
| glyceryl monostearate | 2 | 2 | 2 |
| POE(40) sorbitan monostearate | 2 | 2 | 2 |
| talc | 8 | 8 | 8 |
| particulate titanium oxide | 7 | 7 | 7 |
| titanium oxide | 5 | 5 | 5 |
| particulate yellow iron oxide | 2 | 2 | — |
| particulate red iron oxide | 0.5 | 0.5 | — |
| yellow iron oxide | — | — | 2 |
| red iron oxide | — | — | 0.5 |
| ion-exchanged water | 45 | 45 | 45 |
| glycerin | 5 | 5 | 5 |
| antiseptic | q.s. | q.s. | q.s. |
| antioxidant | q.s. | q.s. | q.s. |
| perfume | q.s. | q.s. | q.s. |
| moisturizing performance | B | C | C |
| smoothness | A | B | B |
| dusty skin feel | B | C | C |
| uniform finish | A | C | B |
| SPF | 23 | 17 | 14 |

As evident from the results shown in Table 18, the oil-in-water emulsified foundation (Example 16) obtained by a production method employing a batch media-agitating mill according to the invention was excellent in the skin touch, the uniform finish and the UV-protecting effect (SPF value) because of satisfactorily dispersed particulate powders such as particulate titanium oxide, particulate yellow iron oxide, particulate red iron oxide and other powders. On the contrary, the oil-in-water emulsified foundations (Comparative example 14-1 and 14-2) produced only by an ordinary dispersing device such as a homogenizer were poor in terms of the skin touch, the uniform finish and the UV-protecting effect (SPF value) when compared with the inventive oil-in-water emulsified foundation because of insufficiently dispersed powders including the particulate powders described above. While particulate powder is known to be more effective than ordinary powders, no substantial improvement of Comparative example 14-1 over Comparative example 14-2 indicates that a oil-in-water foundation produced by an ordinary method can not fully exert the effect of the particulate powder.

EXAMPLE 17

COMPARATIVE EXAMPLE 15-1, 15-2

Oil-in-Water Emulsified Foundation

Table 19 shows a Oil-in-water foundation as Example 17 produced by a production method of the invention. To the aqueous components in the formulation indicated below, the oil components were added and the formulation in the tank was mixed by the disper while emulsifying by the media-agitating mill. Subsequently, hydrophobicity-imparted powders were mixed for 10 minutes by a disper fitted in a batch media-agitating mill, and then a basket part containing zirconia beads each in 1 mm in diameter was driven to disperse and mix the formulation for 30 minutes to obtain a foundation. On the other hand, Comparative example 15-1 and 15-2 employed an ordinary production method. In Comparative example 15-1, the powder components in the formulation identical to that in Example 17 were added to the aqueous components, dispersed by a homogenizer for 10 minutes, combined with the oil components and emulsified by the homogenizer to obtain a sunscreen. In Comparative example 15-2, a foundation was obtained by a method similar to that in Comparative example 15-1 except for using an ordinary iron oxide instead of the particulate powder.

TABLE 19

| | Example | Comparative example | |
|---|---|---|---|
| Oil-in-Water emulsified foundation | 17 | 15-1 | 15-2 |
| squalane | to 100 | to 100 | to 100 |
| olive oil | 5 | 5 | 5 |
| octylmethoxy cinnamate | 5 | 5 | 5 |
| stearic acid | 2 | 2 | 2 |
| glyceryl monostearate | 2 | 2 | 2 |
| POE(40) sorbitan monostearate | 2 | 2 | 2 |
| silicone-treated talc | 8 | 8 | 8 |
| aluminium stearate-treated-particulate titanium oxide | 7 | 7 | 7 |
| silicone-treated particulate yellow iron oxide | 2 | 2 | — |
| silicone-treated particulate red iron oxide | 0.5 | 0.5 | — |
| silicone-treated yellow iron oxide | — | — | 2 |
| silicone-treated red iron oxide | — | — | 0.5 |
| ion-exchanged water | 45 | 45 | 45 |
| glycerin | 5 | 5 | 5 |
| antiseptic | q.s. | q.s. | q.s. |
| antioxidant | q.s. | q.s. | q.s. |
| perfume | q.s. | q.s. | q.s. |
| moisturizing performance | B | C | C |
| smoothness | A | B | B |
| dusty skin feel | B | C | C |
| uniform finish | A | C | B |
| SPF | 29 | 20 | 17 |

As evident from the results shown in Table 19, the oil-in-water emulsified foundation (Example 17) obtained by a production method employing a batch media-agitating mill according to the invention was excellent in the skin touch, the uniform finish and the UV-protecting effect (SPF value) because of satisfactorily dispersed particulate powders such as aluminium stearate-treated particulate titanium oxide, silicone-treated particulate yellow iron oxide, silicone-treated particulate red iron oxide and other powders. On the contrary, the oil-in-water emulsified foundations (Comparative example 15-1 and 15-2) produced only by an ordinary dispersing device such as a homogenizer were poor in terms of the skin touch, the uniform finish and the UV-protecting effect (SPF value) when compared with the inventive oil-in-water emulsified foundation because of insufficiently dispersed particulate powders described above. While particulate powder is known to be more effective than ordinary powders, no substantial improvement of Comparative example 15-1 over Comparative example 15-2 indicates that a oil-in-water foundation produced by an ordinary method can not fully exert the effect of the particulate powder.

EXAMPLE 18

COMPARATIVE EXAMPLE 16

Oil-in-Water Emulsified Foundation

Table 20 shows a oil-in-water foundation as Example 18 produced by a production method of the invention. The powder component and the aqueous components in the formulation indicated below were mixed for 10 minutes by a disper fitted in a batch media-agitating mill, and then a basket part containing zirconia beads each in 1 mm in diameter was driven to disperse and mix the formulation for 30 minutes. Then oil components were added and the formulation in the tank was mixed by the disper while emulsifying by the media-agitating mill to obtain a foundation. On the other hand, Comparative example 16 employed an ordinary production method. The powder components in the formulation identical to that in Example 18 were ground twice by a pulverizer, added to the aqueous components, dispersed by a homogenizer for 10 minutes, combined with the oil components and emulsified by the homogenizer to obtain a foundation.

TABLE 20

| oil-in-water emulsified foundation | Example 18 | Comparative Example 16 |
|---|---|---|
| squalane | to 100 | to 100 |
| olive oil | 10 | 10 |
| stearic acid | 2 | 2 |
| glyceryl monostearate | 2 | 2 |
| POE(40) sorbitan monostearate | 2 | 2 |
| talc | 8 | 8 |
| particulate titanium oxide | 7 | 7 |
| titanium oxide | 5 | 5 |
| yellow iron oxide | 1 | 1 |
| red iron oxide | 0.5 | 0.5 |
| ion-exchanged water | 45 | 45 |
| glycerin | 5 | 5 |
| antiseptic | q.s. | q.s. |
| antioxidant | q.s. | q.s. |
| perfume | q.s. | q.s. |
| moisturizing performance | B | C |
| smoothness | A | B |
| dusty skin feel | B | C |
| uniform finish | A | C |
| SPF | 23 | 17 |

As evident from the results shown in Table 20, the oil-in-water emulsified foundation (Example 18) obtained by a production method employing a batch media-agitating mill according to the invention was excellent in the skin touch, the uniform finish and the UV-protecting effect (SPF value) because of a satisfactorily dispersed particulate powder which was particulate titanium oxide and other powders. On the contrary, the oil-in-water emulsified foundation (Comparative example 16) produced only by an ordinary dispersing device such as a homogenizer was poor in terms of the skin touch, the uniform finish and the UV-protecting effect (SPF value) when compared with the inventive oil-in-water emulsified foundation because of insufficiently dispersed powders described above.

Subsequently, the inventors compared a batch media-agitating mill fitted with a disper and a conventional continuous media-agitating mill (Dino-mill).

The time periods required for milling 350 L in total of powder carbon mixed resin into the particle sizes of 5 μm and 2.5 μm are shown in Table 21. Each of the two media-agitating mills contained as a solid dispersion medium a titania bead whose diameter was 1.6 mm.

TABLE 21

| Production machine | Particle size (μm) | Number of passes | Time (hr) |
|---|---|---|---|
| Continuous media-agitating mill | 5 | 1 | 4 |
| | 2.5 | 2 | 8 |
| Batch media-agitating mill | 5 | — | 1.5 |
| | 2.5 | — | 1.75 |
| (Operating conditions) | | | |
| Continuous media-agitating mill | Charged bead = 80% Output = 86 (kg/h) Circumferential speed = 13 (m/sec) | | |
| Batch media-agitating mill | Charged bead = 85% Circumferential speed = 11 (m/sec) | | |

As evident from the results shown in Table 21, the batch media-agitating mill according to the invention required 1.5 hours and 1.75 hours for milling the powder carbon into the particle sizes of 5 μm and 2.5 μm, respectively. On the contrary, the continuous media-agitating mill required the times which were as long as 4 hours and 8 hours for milling the powder carbon into the particle sizes of 5 μm and 2.5 μM, respectively. Accordingly, the production time can substantially be reduced by employing a batch system.

The time periods required for milling 300 L in total of powder carbon mixed resin by various media-agitating mills into the particle size of 5 μm are shown in Table 22.

TABLE 22

| Production machine | Time (hr) |
|---|---|
| Continuous Dino-mill (8 passes) | 10 |
| Continuous ball mill | 40 |
| Continuous roll mill | 12~24 |
| Batch media-agitating mill | 2~3 |

As evident from the results shown in Table 22, the production method employing the batch agitating mill required 2 to 3 hours for milling the powder carbon into the particle size of 5 μm. On the contrary, the continuous media-agitating mill required the time as long as 10 to 40 hours. Accordingly, Table 22 indicates that the batch media-agitating mill is extremely effective in reducing the production time.

(Method for Producing Cosmetic Product Involving Hydrophobicity-Imparting Step)

The inventors discovered a method for producing an extremely stable hydrophobicity-imparted powder dispersion from an organically-denatured clay mineral using a media-agitating mill. Accordingly, the inventors subsequently investigated a method for producing an oily cosmetic product and an emulsified cosmetic product utilizing such hydrophobicity-imparted powder dispersion.

A hydrophobicity-imparted powder dispersion and a method for producing cosmetic products utilizing the same are discussed below.

Organic Denaturated Clay Minerals

While an organically-denatured clay mineral employed in the invention includes a variety of materials which can be dispersed and swollen in a hydrophobic medium, one obtained by treating a clay mineral capable of being swollen by water with a cationic surfactant of a quaternary ammonium salt type and a nonionic surfactant is preferred particularly.

A clay mineral capable of being swollen by water may, for example, be one of colloidal hydrated aluminium silicates having a three-layered structure represented by a general formula:

$$(X,Y)_A(Si,Al)_4O_{10}(OH)_2Z_B \cdot nH_2O$$

wherein,
X=Al, $Fe^{III}$, $Mn^{III}$, $Cr^{III}$;
Y=Mg, $Fe^{II}$, Ni, Zn, Li;
Z=K, Na, Ca; and,
A is 2 to 3 and B is ⅓;

and those exemplified concretely are natural or synthetic (in this case the group (OH) in the formula is substituted with a fluorine) montmorillonites such as montmorillonite, saponite and hectolite (Beegum™, Kunipia™, Laponite™ and the like) as well as synthetic micas called sodium silicic mica sodium or lithium teniolite (Dimonite™; TOPY Industry Co., Ltd. and the like).

A cationic surfactant of a quaternary ammonium salt type may, for example, be one represented by a general formula:

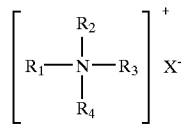

wherein $R_1$ is an alkyl group having 10 to 22 carbon atoms or a benzyl group, $R_2$ is a methyl group or an alkyl group having 10 to 22 carbon atoms, each of $R_3$ and $R_4$ are an alkyl group having 1 to 3 carbon atoms or a hydroxyalkyl group and X is a halogen atom or a methyl sulfate residue.

Those which may be exemplified are dodecyltrimethyl ammonium chloride, mylistyl trimethyl ammonium chloride, cetyltrimethyl ammonium chloride, stearyltrimethyl ammonium chloride, arachyltrimethy ammonium chloride, behenyltrimethyl ammonium chloride, mylistyldimethylethyl ammonium chloride, cetyl dimethylethyl ammonium chloride, stearildimethylethyl ammonium chloride, arachyldimethylethyl ammonium chloride, behenyldimethylethyl ammonium chloride, mylistyldiethylmethyl ammonium chloride, cetyldiethylmethyl ammonium chloride, stearildiethylmethyl ammonium chloride, arachyldiethylmethyl ammonium chloride, behenyldiethylmethyl ammonium chloride, benzyldimethylmylistyl ammonium chloride, benzyldimethylcetyl ammonium chloride, benzyldimethylstealyl ammonium chloride, benzyldimethylbehenyl ammonium chloride, benzylmethylethylcetyl ammonium chloride, benzyl methylethylstealyl ammonium chloride, dibehenyldihydroxyethyl ammonium chloride and corresponding bromides as well as dipalmitylpropylethyl ammonium methyl sulfate.

In the invention, one or more of those listed above may be selected as desired.

A nonionic surfactant employed in an organically-denatured clay mineral has an HLB within the range from 2 to 16, preferably 3 to 12.

An HLB referred-here means a value calculated by Kawakami's equation shown below.

$$HLB = 7 + 11.7 \cdot \log(Mw/Mo)$$

wherein Mw is the molecular weight of a hydrophilic group, and Mo is the molecular weight of a hydrophobic group.

For example, an ether surfactant such as a 2–30 mole polyoxyethylene-additional {hereinafter abbreviated as POE (2–30)} oleyl ether, POE(2–35) stearyl ether, POE (2–20) lauril ether, POE (1–20) alkylphenyl ether, POE (6–18) behenyl ether, POE (5–25) 2-decylpentadecyl ether, POE (3–20) 2-decyltetradecyl ether, POE (3–20) 2-decyltetradecyl ether and POE(8–16) 2-octyldecylether; an ester surfactant such as POE(4–60) hardened castor oil, POE(3–14) fatty acid monoester, POE(6–30) fatty acid diester, POE (5–20) sorbitan fatty acid ester; a surfactant as an ethylene oxide adduct of an ether ester surfactant such as POE(2–30) glyceryl monoisostearate, POE(10–60) glyceryl triisostearate, POE(7–50) hardened castor oil monoisostearate and POE(12–60) hardened castor oil triisostearate; a polyhydric alcohol fatty acid ester surfactant including a polyglycerin fatty acid ester such as decaglyceryl tetraolate, hexaglyceryl triisostearate, tetraglyceryl diisostearate and diglyceryl diisostearate and a glycerin fatty acid ester such as glyceryl monoisostearate and glyceryl monooleate; a nonionic denaturated silicone surfactant such as a denaturated silicone, for example, a dimethylpolysiloxane polyoxyalkylene copolymer represented by Formula:

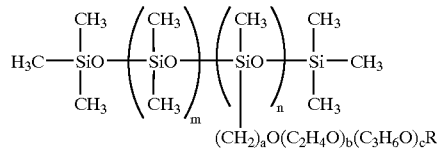

wherein a is 1 to 5, b is 7 to 15, c is 0 to 4, m is 20 to 100, n is 1 to 5, all being an integer, and R is a hydrogen atom or an alkyl group having 1 to 5 carbon atoms.

Among those listed above, a fatty acid ester of triglycerin or higher polyglycerins such as decaglyceryl tetraolate, hexaglyceryl triisostearate, and tetraglyceryl diisostearate and a nonionic surfactant as an ethylene oxide adduct including a POE adduct ether surfactant such as POE (2~12) oleil ether, POE (3~12) stearil ether, POE (2~10) lauril ether, POE (2~10) nonylphenyl ether, POE (6~15) behenyl ether, POE (5~20) 2-decylpentadecyl ether, POE (5~17) 2-decyltetradecyl ether, POE(8~16) 2-octyldecylether; a POE adduct ester surfactant such as POE(10–20) hardened castor oil, POE(5–14) oleic acid monoester, POE(6–20) oleic acid diester and POE(5–10) sorbitan oleic acid ester; a POE adduct ether ester surfactant such as POE(3–15) glyceryl monoisostearate and POE(10–40) glyceryl triisostearate are preferred particularly.

In the invention, one or more of the nonionic surfactants listed above may be selected as desired.

In a treatment for organically-denatured clay mineral, a clay mineral capable of being swollen by water, a cationic surfactant of a quaternary ammonium salt type and a nonionic surfactant are dispersed and agitated in a solvent whose boiling point is low such as water, acetone or a lower alcohol, or a clay mineral capable of being swollen by water and a cationic surfactant of a quaternary ammonium salt type are treated previously in a solvent whose boiling point is low to obtain a cation-denaturated clay mineral which is then treated with a nonionic surfactant and then made free from the solvent whose boiling point is low.

An organically-denatured clay mineral prepared as described above is discussed below. Among the clay minerals, a Na-type montmorillonite which belongs to smectites and is swollen by water is converted into a hydrophobic organically-denatured montmorillonite by a cation exchange reaction with an organic cation of a quaternary ammonium salt type. In addition, an inclusion of a nonionic surfactant results in a formation of an inclusion compound (complex), which is swollen in an oil to form a viscous oily gel. A nonionic surfactant is considered to be included in a polar site of the montmorillonite layer interstice (silicate layer) which is not involved in a cation exchange reaction, and this interstice is invaded further by an oil to undergo a swelling and a gelation, resulting in a formation of an oily gel (YUKAGAKU, Vol. 40, No. 6, 491–496, 1991).

The structure of a resultant organically-denatured clay mineral is characterized by the insertion of a cationic surfactant of a quaternary ammonium salt type and a nonionic surfactant into an interstice which leads to a widened interval between the layers of a clay mineral capable of being swollen by water. Accordingly, the adsorption of the cationic surfactant of the quaternary ammonium salt type and a nonionic surfactant can be identified by determining the interval of the long faces by means of X-ray diffraction.

Also since a Soxlet extraction of a resultant organically-denatured clay mineral with chloroform or ether allows the surfactant in the interstice to be washed out, the presence of the surfactant can be verified by subjecting the extract to a gas chromatography, a thermal decomposition temperature analysis or a thermogravimetric analysis (DTA-TG analysis).

While the amount of a cationic surfactant of the quaternary ammonium salt type in an organically-denatured clay mineral employed in the invention is not particularly limited, it is preferably 60 to 140 milliequivalent (hereinafter abbreviated as meq) per 100 g of a clay mineral capable of being swollen by water. The amount of a nonionic surfactant in an organically-denatured clay mineral is preferably 5 to 100 g, more preferably 15 to 50 g per 100 g of a clay mineral capable of being swollen by water.

The amount of an organically-denatured clay mineral employed is preferably 0.1 to 5%, more preferably 0.5 to 3% in a dispersion. An amount less than 0.1% results in a difficulty in allowing the effect of the addition of an organically-denatured clay mineral to be exerted and also in obtaining a stable dispersion. On the other hand, an amount exceeding 5% results in a higher viscosity of the dispersion obtained, which leads to an excessive load when exerting a high sheer force and poses a practical problem such as a poor extension, a dusty feel or an absence of transparency after incorporation into a composition such as cosmetic products.

Hydrophobic Dispersion Medium

In the invention, it is required that an organically-denatured clay mineral obtained as described above is dispersed and swollen by incorporating into a hydrophobic dispersion medium. Examples of such hydrophobic dispersion medium are a hydrocarbon oil such as liquid paraffin, squalane, isoparaffin and branched chain light paraffin, an ester oil such as isopropyl myristate, cetyl isooctanoate and glyceryl trioctanoate and a silicone oil such as decamethyl pentasiloxane, dimethylpolysiloxane and methylphenyl polysiloxane.

In the invention, a silicone-based oil fraction is employed preferably, with one whose boiling point at normal pressure is 200° C. or less being preferred for a better skin touch and from a pharmaceutical point of view. Examples are a linear polysiloxane such as dimethylpolysiloxane, methylphenyl polysiloxane and methyl hydrogen polysiloxane, and a cyclic polysiloxane such as octamethyl cyclotetrasiloxane, decamethyl cyclopemtasiloxane, dodecamethyl cyclohexasiloxane and tetramethyl tetrahydrogen cyclotetrasiloxane. Among those listed above, a volatile silicone oil including a volatile linear polysiloxane such as a dimethylpolysiloxane having a low degree of polymerization (degree of polymerization: 3 to 7), a cyclic volatile polysiloxane such as decamethyl cyclopentasiloxane and octamethyl cyclotetrasiloxane is employed preferably for obtaining a light skin touch since it gives a reduced oily touch sustaining on a skin when compared with an ordinary silicone oil.

While the amount of a hydrophobic dispersion medium to be incorporated in a dispersion of the invention may vary appropriately, it is preferably 40 to 95% by weight, especially 50 to 80% by weight. A smaller amount of a dispersion medium leads to an excessive load when exerting a high sheer force, while a larger amount of a dispersion medium leads to a relatively low rate of a particle, resulting in a reduced significance as a hydrophobic particulate dispersion.

Surfactant

A surfactant employed preferably in the invention is not particularly limited as long as it can disperse an organically-denatured clay mineral satisfactorily in a dispersion medium. Examples are sorbitan sesquiisostearate, sorbitan diisostearate, sorbitan sesquioleate, sorbitan dioleate, glyceryl dioleate, glyceryl diisostearate, polyoxyalkylene-denaturated organopolysiloxane and the like. When a silicone-based dispersion medium is employed as a dispersion medium, it is preferable to use a silicone-based surfactant such as a polyoxyethylene-methylpolysiloxane copolymer.

A surfactant according to the invention is present in a dispersion medium in an amount preferably of 0.1 to 5% by weight, a smaller amount than which may lead to an insufficiently dispersed or swollen organically-denatured clay mineral while a larger amount than which may not give a correspondingly increased improvement.

Particle which is Not Made Hydrophobic

A particle which is not made hydrophobic in the invention includes a variety of particles employed in a cosmetic formulation each having a hydrophilic surface.

Such powder component in the invention may, for example, be an inorganic powder such as titanium oxide, zinc oxide, aluminum oxide, zirconium oxide, red iron oxide, yellow iron oxide, black iron oxide, ultramarineblue, cerium oxide, talc, mica, sericite, kaolin, silica, zinc stearate, fluorine phlogopite, synthesis talc, barium sulfate, magnesium carbonate, boron nitride, and titanates; an inorganic white pigment such as titanium oxide and zinc oxide; an inorganic colored pigment such as red iron oxide, yellow iron oxide, black iron oxide, carbon black, titanium black, manganese violet, cobalt violet, ultramarineblue, and prussian blue; a pearl pigment such as titanium oxide coated mica, titanium oxide coated talc, coloring titanium oxide coated mica, bismuth oxychloride, and scale powder and a metal powder pigment such as alumina.

Also in the invention, an organic or inorganic particle coated with an oxide or a hydrated oxide of aluminium, silicon, titanium, zirconium, magnesium or zinc can also be employed.

Powder doped with other elements or a composite oxide of two or more metals may also be employed.

Furthermore, a zinc oxide particle having a 1 to 3 nm silica layer formed by coating the zinc oxide with 10 to 30% by weight of tetraethoxysilane may also be employed preferably as powder component.

A dispersion of the invention is effective particularly in a UV-protecting particle. Such UV-protecting particle may, for example, be zinc oxide, iron oxide, cerium oxide and titanates.

Also in view of the fact that a dispersion of the invention is effective especially in particulate powder having an excellent UV-protecting effect, one which can be exemplified is particulate powder whose mean particle size is 0.001 to 0.5 $\mu$m selected from particulate titanium oxide, particulate zinc oxide, particulate red iron oxide, particulate yellow iron oxide, particulate black iron oxide, particulate cobalt blue and the like. Particulate powder is known to be more excellent in the UV-protecting effect and the transparency when compared with an ordinary powder.

One or more of these particulate powder are contained in a dispersion in an amount preferably of 5 to 50% by weight, more preferably 10 to 35% by weight. An amount less than 5% by weight may lead to a difficulty in exerting the effect of particulate powder, while an amount exceeding 40% by weight may result in an excessive load when exerting a high sheer force.

Particle Coating Agent

While a particle coating agent employed preferably in the invention is not particularly limited, it should be dispersible in a non-aqueous solvent described above such as a silicone-based compound including dimethylpolysiloxane-methyl (polyoxyalkylene) siloxane copolymer, trimethyl siloxysilicic acid, a carboxy-denaturated silicone oil and amino-denaturated silicone oil. Such silicone-based particle coating agent is incorporated in an amount preferably of 1 to 40% by weight, more preferably 5 to 30% by weight based on a particle.

Media-Agitating Mill Processing

In the invention, it is required to perform a media-agitating mill processing in order to disperse a particle into a state of a primary particle or close to a primary particle in the essential components described above, and for performing such media-agitating mill processing it is preferable to use a media-agitating mill of batch type, continuous lateral type, vertical type and annular type.

A batch media-agitating mill which is a dispersing device employed preferably in a production method of the invention was described in the section of a method for producing cosmetic products containing particulate powder described above. Accordingly, a continuous media-agitating mill employed in the invention is discussed below.

A continuous media-agitating mill in the invention is provided separately with a media mill part and a preliminary stirring tank. The media mill part has a solid dispersion medium such as a bead contained in a container in which a stirring device for stirring the content is provided. The preliminary stirring tank is provided with a stirring device. The preliminary stirring tank and the media mill part are in communication with each other via a pipe in which a fluid containing a particle travels. Accordingly, when a cosmetic starting-material containing a particle is introduced, it is stirred in the preliminary stirring tank and then pumped to the media mill part. When the content of the container is stirred in the media mill part, the solid dispersion medium is also stirred together with the particle. Then the stirred solid dispersion medium can further grind and disperse an aggregated particle of the powder components. In a continuous media-agitating mill, a circulation between the media mill part and the preliminary stirring tank is possible if necessary. As a result, the continuous media-agitating mill enables cosmetic production involving a step for imparting a particle with hydrophobicity within a single device.

A continuous media-agitating mill employed preferably in the invention is detailed below. FIG. 2 shows an example of a continuous media-agitating mill fitted with a preliminary stirring tank. In the continuous media-agitating mill device shown in FIG. 2, media mill part 30 containing beads 40 capable of being agitated by the rotation of motor 36 is connected through a pipe via pump 34 with preliminary stirring tank 32 capable of stirring by means of disper 42 driven by the rotation of motor 38, whereby allowing a fluid containing a particle to be circulated.

First, a starting material containing a particle is mixed preliminary by disper 42 in preliminary stirring device 32 to form a fluid mixture, which is pumped by pump 34 into media mill part 30 connected through a pipe.

The fluid mixture introduced into media mill part 30 is brought into contact with a rotating stirrer which rotates at a high speed and pulverizes and disperses various aggregated particles of the powder components in cooperation with solid dispersing media (beads) 40 and then pumped by pump 34 back into preliminary stirring tank 32.

A continuous media-agitating mill means a device having a step for making the dispersion of particles uniform as described above. The stirring time in the preliminary stirring tank, the stirring time in the media mill part and the number of passes in this device are determined appropriately as desired.

While the stirring device of a preliminary stirring tank employed preferably in the invention may be a stirring device suitable in an ordinary cosmetic production, it is especially preferable to use a disper or a homogenizer having a turbinal blade on the tip of a rotating rod. A biaxial disper having a disper fin and a scraping fin is also employed preferably.

A step for obtaining a hydrophobicity-imparted particle dispersion according to the invention and a method for producing cosmetic products containing such particle are further detailed below with referring to examples.

Step for Obtaining Hydrophobicity-Imparted Particle Dispersion and Method for Producing Cosmetic Product When using a batch media-agitating mill containing a stirring device in a tank, a batch media-agitating mill having an in-tank stirring device is employed to mix a dispersion medium such as a silicone oil with an organically-denatured clay mineral and a surfactant by the in-tank stirring device and then the formulation is dispersed and mixed for example for 3 to 10 minutes by a basket part as a media mill part and then supplemented with powder which is not made hydrophobic such as titanium oxide and a particle coating agent such as trimethyl siloxysilicic acid, and then further dispersed and mixed by a high sheer force for a longer time such as 10 minutes to 10 hours. During this time period, titanium oxide described above is coated with trimethyl siloxysilicic acid to form a hydrophobicity-imparted titanium oxide. As a result, a hydrophobicity-imparted particle dispersion can be produced within a short period at a low cost in a single tank. In addition, a washing step after the production can substantially be simplified when compared with a conventional production. Moreover, by combining this hydrophobicity-imparted particle dispersion in the media-agitating mill directly with other oils and particles followed by filling in a certain mold, an oily cosmetic product can be obtained. Since a hydrophobicity-imparted particle is contained, an oily cosmetic product such as an oily foundation exhibits a smooth and light texture and gives a clear finish together with a high UV-protecting effect.

Also when a continuous media-agitating mill fitted with a preliminary stirring device is employed, a dispersion medium such as a silicone oil is stirred and mixed in the preliminary stirring device, and then powder which is not made hydrophobic such as titanium oxide and a particle coating agent such as trimethyl siloxysilicic acid are added to the preliminary stirring tank and stirred and mixed for a short period such as 3 to 10 minutes and then dispersed and mixed by a high sheer force and a high impact force in the media mill part for a long time such as 10 minutes to 10 hours, or 3 to 10 passes, or 3 passes to 10 minutes. During this time period, the particle which is not made hydrophobic such as titanium oxide described above is coated with trimethyl siloxysilicic acid to form a hydrophobicity-imparted titanium oxide.

A hydrophobicity-imparted particle dispersion can be obtained also by adding a particle which is not made hydrophobic and a particle coating agent to a dispersion medium initially together with an organically-denatured clay mineral and the like.

Also in an example of a method for producing an emulsified cosmetic product, a batch media-agitating mill having an in-tank stirring device is used, in the case of a water-in-oil emulsified cosmetic product, to prepare a hydrophobicity-imparted particle dispersion as described above, which is then supplemented with aqueous component to form a dispersion which is stirred in the tank by a mixing stirring part while effecting an emulsification by means of the media-agitating mill to obtain the water-in-oil emulsified cosmetic product. Alternatively, after preparing a dispersion described above, aqueous components are added and mixed and phase-transferred by an in-tank stirring device and then dispersed and mixed in a basket part as a media mill part, and then supplemented with oil components to form a dispersion which is stirred in the tank by a mixing stirring device while effecting an emulsification by means of the media-agitating mill to obtain the oil-in-water emulsified cosmetic product. According to this method, an emulsified cosmetic product containing a hydrophobicity-imparted particle can be produced in a single device continuously within a short time by a simple operation at a low cost. Moreover, an emulsified cosmetic product containing a hydrophobicity-imparted particle obtained according to the invention exhibits a high UV-protecting effect because of a high dispersibility as well as a smooth and creamy texture resulted from the emulsifying step using a media-agitating mill.

Other Components

When preparing cosmetic products in the invention, a hydrophobicity-imparted particle dispersion described above may further be combined with an oil component. Such oil component is not particularly limited as long as it is employed in cosmetic production, and may, for example, be an ester oil such as cetyl isooctanoate, glyceryl trihexanoate and isopropyl myristate, a hydrocarbon-based oil fraction such as vaseline, liquid paraffin and squalane and a naturally occurring animal and plant oil such as castor oil, olive oil, camellia oil, jojoba oil and lanolin, which may be employed appropriately in combination.

When producing a solid oily cosmetic product according to the invention, a wax component is preferably be incorporated as a solidifying agent. A wax component as a solidifying agent may, for example, be microcrystalline wax, carnauba wax, candelilla wax, polyethylene wax, ceresin wax and the like, which may be used in combination. The wax components are contained preferably in an amount of 3 to 25% by weight in total.

An aqueous component in the invention may, for example, be a polyhydric alcohol such as glycerin, a water-soluble material such as ethyl alcohol as well as water.

A cosmetic product according to the invention may further contain surfactants, dispersants, stabilizers, colorants, antiseptics, antioxidants, UV absorbers, humectants, perfumes and the like appropriately as long as the objectives of the invention are accomplished.

Utility

A production method according to the invention may be applied, for example, to oily cosmetic products such as eyeliner pencils, eyebrow pencils, oily foundations, oily stick foundations and oily eye colors as well as emulsified cosmetic products such as emulsified sunscreen and emulsified foundation.

Other Effects

A cosmetic product containing a dispersion according to the invention exhibits an excellent UV-shielding effect attributable to a UV-protecting particulate which had highly been dispersed as described above together with an advantageous characteristics such as satisfactory skin touch, water resistance and oil resistance as well as excellent emulsion stability and chemical stability.

A step for obtaining a hydrophobicity-imparted particle of the invention and a method for producing cosmetic products containing such particle are further detailed below with referring to examples. The inventors investigated a method for imparting a particle in cosmetic products with hydrophobicity. First, the inventors prepared hydrophobicity-imparted particle dispersions by various methods and evaluated the dispersions. The results are shown in Table 23.

TABLE 23

| dispersing element | experiment | | | | |
|---|---|---|---|---|---|
|  | 6 | 7 | 8 | 9 | 10 |
| volatile silicone | 61 | 61 | 60 | 60 | 60 |
| methylpolysiloxane | 5 | 5 | 5 | 5 | 5 |
| polyoxyethylene-methylpolysiloxane copolymer | 1 | 1 | 1 | 1 | 1 |
| organically-denatured bentonite | 0 | 0 | 1 | 1 | 1 |
| particulate zinc oxide | 25 | 25 | 25 | 25 | 25 |
| trimethyl siloxysilicic acid | 8 | 8 | 8 | 8 | 8 |
| method for produce | A | B | A | B | C |
| Separation (room temperature) |  |  |  |  |  |
| Immediately after production | A | A | A | A | A |
| After 4 weeks | B | B | A | A | C |
| viscosity (room temperature) |  |  |  |  |  |
| Immediately after production | 480 | 520 | 650 | 710 | 155 |
| After 4 weeks | 300 | 280 | 410 | 380 | 60 |

The separation was evaluated in accordance with the following criteria.

A: Almost no sedimentation of the powders is observed.
B: Although the sedimentation of the powders is observed, it can readily be dispersed again.
C: The powders undergo the sedimentation and the caking makes it difficult to disperse them again.

Production method A: All components are mixed and dispersed for 55 minutes by a media-agitating mill.

Production method B: Volatile silicone, methylpolysiloxane, polyoxyethylene-methylpolysiloxane copolymer and organically-denatured bentonite are premixed (for 5 minutes by a media-agitating mill) and combined with a particulate zinc oxide and trimethyl siloxysilicic acid, and the mixture is dispersed by the media-agitating mill for 50 minutes.

Production method C: Volatile silicone, methylpolysiloxane, polyoxyethylene-methylpolysiloxane copolymer and organically-denatured bentonite are premixed (for 5 minutes by a disper) and combined with a particulate zinc oxide and trimethyl siloxysilicic acid, and the mixture is dispersed for 50 minutes by a disper employed ordinarily for producing cosmetic products.

As evident from Table 23 shown above, any method imparted the particulate zinc oxide with almost no hydrophobicity when using no organically-denatured clay mineral (Experiments 6 and 7), and underwent the separation and the reduction in the viscosity over a time period. Also when using an ordinary disper which exerts a low sheer force for dispersing the formulation (Experiment 10), the stability was poor in spite of the addition of the organically-denatured clay mineral. On the contrary, each of the systems employing the organically-denatured clay mineral to which the particulate zinc oxide and trimethyl siloxysilicic acid were added and a high sheer force was exerted by the media-agitating mill (Experiments 8 and 9) exhibited an excellent stability, and an extremely high stability was observed especially in the case where the organically-denatured clay mineral had previously been converted into a gel to which then the particulate zinc oxide and trimethyl siloxysilicic acid were added (Experiment 9).

The inventors subsequently employed the dispersions of Experiments 6 to 10 to prepare and evaluate water-in-oil emulsified compositions. The results are shown in

TABLE 24

|  |  | experiment | | | | |
| --- | --- | --- | --- | --- | --- | --- |
|  |  | 11 | 12 | 13 | 14 | 15 |
| dispersing element | experiment 6 | 60 | — | — | — | — |
|  | experiment 7 | — | 60 | — | — | — |
|  | experiment 8 | — | — | 60 | — | — |
|  | experiment 9 | — | — | — | 60 | — |
|  | experiment 10 | — | — | — | — | 60 |
| nylon powder |  | 5 | 5 | 5 | 5 | 5 |
| octyl methoxy cinnamate |  | 7 | 7 | 7 | 7 | 7 |
| polyoxyethylene-methyl-polysiloxane copolymer |  | 0.5 | 0.5 | 0.5 | 0.5 | 0.5 |
| isostearic acid |  | 0.5 | 0.5 | 0.5 | 0.5 | 0.5 |
| moisturizing element |  | 5 | 5 | 5 | 5 | 5 |
| ion-exchanged water |  | to 100 | | | | |
| viscosity (room temperature) |  |  |  |  |  |  |
| Immediately after production |  | 675 | 810 | 1040 | 1160 | 310 |
| After 4 weeks |  | 540 | 660 | 930 | 1070 | 205 |
| smoothness |  | B | B | B | B | D |
| dusty skin feel |  | B | B | B | B | D |
| uniform finish |  | C | C | B | B | D |
| whiteness when applied |  | C | C | B | B | D |
| SPF |  | 41 | 43 | 49 | 51 | 30 |

An organoleptic test was conducted to evaluate the dusty skin feel, the uniform finish and the transparency, and the SPF values were also determined. The criteria described below were employed in the evaluation.

Evaluation Criteria

20 Female panelists received the application of a test formulation and evaluated the formulation with regard to the smoothness, the dusty skin feel, the uniform finish and the transparency.

<Evaluation>

| 17 Panelists or more judged as good. | A |
| --- | --- |
| 12 to 16 Panelists judged as good. | B |
| 9 to 11 Panelists judged as good. | C |
| 5 to 8 Panelists judged as good. | D |
| 4 Panelists or less judged as good. | E |

A formulation was obtained by combining each dispersion with a nylon powder, octylmethoxy cinnamate, polyoxyethylene-methylpolysiloxane copolymer and isostearic acid, and stirred and mixed by a disper for 2 minutes, combined further with a humectant and ion-exchange water, stirred and mixed further for 2 minutes by the disper. Each of these water-in-oil sunscreens was examined for its smoothness, dusty skin feel, uniform finish and whiteness when applied by an organoleptic test, and its SPF value was also determined.

As evident from Table 24 shown above, each of Experiments 11, 12 and 15 in which the particulate zinc oxide had not been considered to be imparted with hydrophobicity not only exhibited a poor stability but also was evaluated to be a poor cosmetic product. On the contrary, all of the cosmetic products according to the invention (Experiments 13 and 14) exhibited excellent effects. Since this test employed a zinc oxide which was not imparted with hydrophobicity and thus was not made hydrophobic, an insufficiently imparted hydrophobicity resulted in an aggregation of the powders and a low SPF value.

Based on the results shown in Tables 23 and 24, it can be understood that a dispersion according to the invention not only had an improved dispersibility of the particulate zinc oxide but also allowed the surface of the particulate-zinc oxide to be coated and imparted with hydrophobicity and that for the purpose of allowing the particulate zinc oxide to be coated with trimethyl siloxysilicic acid and imparted with hydrophobicity the presence of the organically-denatured clay mineral and the exertion of a high sheer force by the media-agitating mill are essential.

The inventors subsequently investigated the amount of an organically-denatured clay mineral when producing a dispersion. The results are shown in Table 25.

TABLE 25

|  | experiment | | | | | | | |
| --- | --- | --- | --- | --- | --- | --- | --- | --- |
| dispersing element | 16 | 17 | 18 | 19 | 20 | 21 | 22 | 23 |
| volatile silicone | 61.0 | 60.9 | 60.5 | 60.0 | 59.5 | 58.0 | 56.0 | 54.0 |
| methylpolysiloxane | 5.0 | 5.0 | 5.0 | 5.0 | 5.0 | 5.0 | 5.0 | 5.0 |

TABLE 25-continued

|  | experiment | | | | | | | |
| --- | --- | --- | --- | --- | --- | --- | --- | --- |
| dispersing element | 16 | 17 | 18 | 19 | 20 | 21 | 22 | 23 |
| polyoxyethylene-methylpolysiloxane copolymer | 1.0 | 1.0 | 1.0 | 1.0 | 1.0 | 1.0 | 1.0 | 1.0 |
| organically-denatured bentonite | 0 | 0.1 | 0.5 | 1.0 | 1.5 | 3.0 | 5.0 | 7.0 |
| particulate zinc oxide | 25.0 | 25.0 | 25.0 | 25.0 | 25.0 | 25.0 | 25.0 | 25.0 |
| trimethyl siloxysilicic acid | 8.0 | 8.0 | 8.0 | 8.0 | 8.0 | 8.0 | 8.0 | 8.0 |
| manufacture by media-agitating mil | B | A | A | A | A | A | B | C |

The producibility was evaluated based on the criteria shown below.

A: The powder can satisfactorily be dispersed by the media-agitating mill.

B: In response to an increased viscosity or an aggregation of the powder, the dispersing performance by the media-agitating mill may become somewhat poor.

C: An increased viscosity makes it impossible to disperse by the media-agitating mill.

As evident from Table 25 shown above, the effect of the organically-denatured clay mineral began to be observed at a concentration of about 0.1%, but a concentration close to 7% was rather undesirable due to a too high viscosity.

Accordingly, the amount of an organically-denatured clay mineral when subjected to a media-agitating mill is 0.1% by weight to 5% by weight, preferably 0.5 to 3.0% by weight.

The inventors subsequently investigated the amount of a particle to be added. The results are indicated in Table 26 shown below.

TABLE 26

|  | experiment | | | | | | | | |
| --- | --- | --- | --- | --- | --- | --- | --- | --- | --- |
| dispersing element | 24 | 25 | 26 | 27 | 28 | 29 | 30 | 31 | 32 |
| volatile silicone | 86.4 | 79.8 | 73.2 | 66.6 | 60.0 | 53.4 | 40.2 | 27.0 | 13.8 |
| methylpolysiloxane | 5.0 | 5.0 | 5.0 | 5.0 | 5.0 | 5.0 | 5.0 | 5.0 | 5.0 |
| polyoxyethylene-methylpolysiloxane copolymer | 1.0 | 1.0 | 1.0 | 1.0 | 1.0 | 1.0 | 1.0 | 1.0 | 1.0 |
| organically-denatured bentonite | 1.0 | 1.0 | 1.0 | 1.0 | 1.0 | 1.0 | 1.0 | 1.0 | 1.0 |
| particulate zinc oxide | 5.0 | 10.0 | 15.0 | 20.0 | 25.0 | 30.0 | 40.0 | 50.0 | 60.0 |
| trimethylsiloxysilicic acid | 1.6 | 3.2 | 4.8 | 6.4 | 8.0 | 9.6 | 12.8 | 16.0 | 19.2 |
| manufacture by media-agitating mil | A | A | A | A | A | A | B | C | C |
| viscosity (room temperature) | | | | | | | | | |
| Immediately after production | 45 | 50 | 210 | 445 | 710 | 990 | 4350 | 12600 | 65100 |
| After 4 weeks | 25 | 25 | 95 | 280 | 380 | 475 | 3860 | 10800 | 61400 |

As evident from Table 26 shown above, the particle added at 50% was not preferable since it raised the viscosity during the preparation excessively and the load on the media-agitating mill became greater markedly. On the other hand, the particle had almost no effect on the stability when added in a small amount, but it is preferable for the purpose of supplying the hydrophobicity-imparted particles to other compositions efficiently that the amount is 5 to 50% by weight.

The inventors subsequently investigated, based on the technologies discussed above, a method for producing cosmetic products in which a hydrophobicity imparting step and an emulsifying step are conducted continuously.

First, the inventors prepared an emulsified cosmetic product containing a hydrophobicity-imparting particle by a production method described below and investigated the stability over a time period. An organoleptic test was also conducted to evaluate the dusty skin feel, the uniform finish and the transparency, and the SPF values were also determined. The criteria employed in the evaluation are as described above.

The results are shown in Table 27.

TABLE 27

|  | Experiment | | | |
| --- | --- | --- | --- | --- |
| sunscreen | 33 | 34 | 35 | 36 |
| (oil phase) | | | | |
| volatile silicone | 36 | 36 | 36 | 36 |
| methylpolysiloxane | 3 | 3 | 3 | 3 |
| polyoxyethylene-methylpolysiloxane copolymer | 0.6 | 0.6 | 0.6 | 0.6 |
| organically-denatured bentonite | 0.6 | 0.6 | 0.6 | 0.6 |
| particulate zinc oxide | 15 | 15 | 15 | 15 |
| tri-methyle siloxysilicic acid | 4.8 | 4.8 | 4.8 | — |

TABLE 27-continued

|  | Experiment | | | |
| --- | --- | --- | --- | --- |
| sunscreen | 33 | 34 | 35 | 36 |
| (adjucion components) | | | | |
| nylon powder | 5 | 5 | 5 | 5 |
| octylmethoxy cinnamate | 7 | 7 | 7 | 7 |
| polyoxyethylene-methylpolysiloxane copolymer | 0.5 | 0.5 | 0.5 | 0.5 |
| isostearic acid | 0.5 | 0.5 | 0.5 | 0.5 |
| (water phase) | | | | |
| humectant | 5 | 5 | 5 | 5 |
| ion-exchanged water | | to 100 | | |

TABLE 27-continued

| sunscreen | Experiment | | | |
|---|---|---|---|---|
| | 33 | 34 | 35 | 36 |
| Separation (room temperature) | | | | |
| Immediately after production | A | A | A | C |
| After 4 weeks | A | A | B | D |
| smoothness | A | B | C | C |
| dusty skin feel | A | B | D | C |
| uniform finish | A | A | C | D |
| SPF | 48 | 46 | 36 | 33 |

Production method (Experiment 33): Volatile silicone, methylpolysiloxane, polyoxyethylene-methylpolysiloxane copolymer and organically-denatured bentonite are premixed (for 5 minutes by a media-agitating mill) and combined with a particulate zinc oxide and trimethyl siloxysilicic acid, and the mixture is dispersed by the media-agitating mill for 50 minutes (oil phase). Subsequently, to the oil phase in the same tank, nylon powder, octyl methoxycinnamate, polyoxyethylene-methylpolysiloxane copolymer and isostearic acid were added and stirred and mixed by a disper for 5 minutes, combined with a humectant and ion-exchanged water, stirred and mixed further for 5 minutes by the disper, and then emulsified for 5 minutes by the media-agitating mill.

Production method (Experiment 34): Volatile silicone, methylpolysiloxane, polyoxyethylene-methylpolysiloxane copolymer and organically-denatured bentonite are premixed (for 5 minutes by a media-agitating mill) and combined with a particulate zinc oxide and trimethyl siloxysilicic acid, and the mixture is dispersed by the media-agitating mill for 50 minutes (oil phase). Subsequently, to the oil phase in the same tank, a nylon powder, octyl methoxycinnamate, polyoxyethylene-methylpolysiloxane copolymer and isostearic acid were added and stirred and mixed by a homogenizer for 5 minutes, combined with a humectant and ion-exchange water, stirred and mixed further for 5 minutes by a homogenizer whereby emulsifying the formulation.

Production method (Experiment 35): Volatile silicone, methylpolysiloxane, polyoxyethylene-methylpolysiloxane copolymer and organically-denatured bentonite are premixed (for 5 minutes by a media-agitating mill) and combined with a particulate zinc oxide and trimethyl siloxysilicic acid, and the mixture is dispersed by a disper employed ordinarily in producing cosmetic products for 50 minutes (oil phase). Subsequently, to the oil phase in the same tank, nylon powder, octyl methoxycinnamate, polyoxyethylene-methylpolysiloxane copolymer and isostearic acid were added and stirred and mixed by a disper for 5 minutes, combined with a humectant and ion-exchanged water, and then stirred and mixed further for 5 minutes by the disper.

Production method (Experiment 36): A procedure analogous to that in Experiment 33 was employed.

As evident from Table 27 shown above, each of Experiment 35 in which the particulate zinc oxide had not been considered to be imparted with hydrophobicity and Experiment 36 in which no hydrophobicity was imparted exhibited a poor stability and was evaluated to be a poor cosmetic product. On the contrary, each of the cosmetic products according to the invention (Experiments 33 and 34) exhibited an excellent stability and a satisfactory dispersibility of the particles, thus showing excellent effects also in the evaluation of the cosmetic products.

Based on the results shown in Table 27, it can be understood that an emulsified cosmetic product according to the invention not only had an improved dispersibility of the particulate zinc oxide but also allowed the surface of the particulate zinc oxide to be coated and imparted with hydrophobicity and that for the purpose of allowing the particulate zinc oxide to be coated with trimethyl siloxysilicic acid and imparted with hydrophobicity a dispersing operation by the media-agitating mill is essential.

Examples of a method for producing an emulsified cosmetic product involving the hydrophobicity-imparting step according to the invention are described below.

EXAMPLE 19

Water-in-Oil Sunprotect Formulation (Method [1])

Volatile silicone, methylpolysiloxane and organically-denatured clay mineral as oil phase constituent were dispersed by a disper in a batch media-agitating mill for 5 minutes, and combined with a particulate zinc oxide and trimethyl siloxysilicic acid, and the mixture is dispersed by a disper for 5 minutes, and then dispersed by the media mill part for 30 minutes. Thereafter, additive components and an water phase were added and the mixture was dispersed for 5 minutes by the disper, and then dispersed by the media mill part for 5 minutes whereby emulsifying the formulation.

(Method [2])

Volatile silicone, methylpolysiloxane and organically-denatured clay mineral as oil phase constituent were dispersed by a disper in a preliminary stirring tank of a continuous media-agitating mill fitted with the preliminary stirring tank for 5 minutes, and combined with a particulate zinc oxide and trimethyl siloxysilicic acid, and the mixture was dispersed by a disper for 5 minutes, and then dispersed by subjecting to 5 passes in the media mill part. Thereafter, additive components and an water phase were added and the mixture was added to the preliminary stirring tank and dispersed for 5 minutes by the disper, and then subjected to 1 pass in the media mill part, whereby dispersing and emulsifying the formulation.

| (oil phase) | |
|---|---|
| volatile silicone | 30 |
| methylpolysiloxane | 5 |
| polyoxyethylene-methylpolysiloxane copolymer | 0.3 |
| organically-denatured bentonite | 0.3 |
| particulate zinc oxide | 15 |
| tri-methyle siloxysilicic acid | 4.5 |
| (adjucion components) | |
| silicone resin powder | 3 |
| octylmethoxy cinnamate | 7.5 |
| polyoxyethylene-methylpolysiloxane copolymer | 1.2 |
| isostearic acid | 0.5 |
| perfume | q.s. |
| (water phase) | |
| moisturizing element | 5 |
| antiseptic | q.s. |
| ion-exchanged water | to 100 |

EXAMPLE 20

Water-in-Oil Emulsified Foundation (Method [1])

Volatile silicone, methylpolysiloxane and organically-denatured clay mineral as oil phase constituent were dispersed by a disper in a batch media-agitating mill for 5 minutes, and combined with a particulate titanium oxide and trimethyl siloxysilicic acid, and the mixture is dispersed by a disper for 5 minutes, and then dispersed by the media-mill part for 30 minutes. Thereafter, additive components and an water phase were added and the mixture was dispersed for 5 minutes by the disper, and then dispersed by the media mill part for 10 minutes whereby emulsifying the formulation.

(Method [2])

Volatile silicone, methylpolysiloxane and organically-denatured clay mineral as oil phase constituent were dispersed by a disper in a preliminary stirring tank of a continuous media-agitating mill fitted with the preliminary stirring tank for 5 minutes, and combined with a particulate titanium oxide and trimethyl siloxysilicic acid, and the mixture was dispersed by a disper for 5 minutes, and then dispersed by subjecting to 3 passes in the media mill part. Thereafter, additive components and an water phase were added and the mixture was added to the preliminary stirring tank and dispersed for 5 minutes by the disper, and then subjected to 2 passes in the media mill part, whereby dispersing and emulsifying the formulation.

| (oil phase) | |
|---|---|
| volatile silicone | 20 |
| methylpolysiloxane | 15 |
| polyoxyethylene-methylpolysiloxane copolymer | 1 |
| organically-denatured bentonite | 1 |
| particulate titanium oxide (aluminium-treated) | 5 |
| tri-methyl siloxysilicic acid | 1.5 |
| (adjucion components) | |
| nylone powder | 3 |
| silicone treated talc | 10 |
| silicone treated titanium oxide | 8 |
| silicone treated yellow zinc oxide | 2 |
| silicone treated red zinc oxide | 1 |
| silicone treated black zinc oxide | 0.5 |
| polyoxyethylene-methylpolysiloxane copolymer | 1.5 |
| isostearic acid | 0.5 |
| (water phase) | |
| moisturizing element | 8 |
| antiseptic | q.s. |
| ion-exchanged water | to 100 |

EXAMPLE 21

Water-in-Oil Emulsified Foundation (Method [1])

Volatile silicone, methylpolysiloxane and organically-denatured clay mineral as oil phase constituent were dispersed by a disper in a batch media-agitating mill for 5 minutes, and combined with particulate titanium oxide, colorant, loading pigment and trimethyl siloxysilicic acid, and the mixture is dispersed by a disper for 5 minutes, and then dispersed by the media mill part for 30 minutes. Thereafter, additive components and an water phase were added and the mixture was dispersed for 5 minutes by the disper, and then dispersed by the media mill part for 5 minutes whereby emulsifying the formulation.

(Method [2])

Volatile silicone, methylpolysiloxane and organically-denatured clay mineral as oil phase constituent were dispersed by a disper in a preliminary stirring tank of a continuous media-agitating mill fitted with the preliminary stirring tank for 5 minutes, and combined with particulate titanium oxide, colorant, loading pigment and trimethyl siloxysilicic acid, and the mixture was dispersed by a disper for 5 minutes, and then dispersed by subjecting to 3 passes in the media mill part. Thereafter, additive components and an water phase were added and the mixture was added to the preliminary stirring tank and dispersed for 5 minutes by the disper, and then subjected to 2 passes in the media mill part, whereby dispersing and emulsifying the formulation.

| (oil phase) | |
|---|---|
| volatile silicone | 20 |
| methylpolysiloxane | 15 |
| polyoxyethylene-methylpolysiloxane copolymer | 1 |
| organically-denatured bentonite | 1 |
| particulate titanium oxide(aluminum treated) | 5 |
| titanium oxide | 8 |
| yellow iron oxide | 2 |
| red iron oxide | 1 |
| black iron oxide | 0.5 |
| talc | 10 |
| trimethyl siloxysilicic acid | 4.5 |
| (adjucion components) | |
| nylone powder | 3 |
| polyoxyethylene-methylpolysiloxane copolymer | 1 |
| (water phase) | |
| moisturizing element | 8 |
| antiseptic | q.s. |
| ion-exchanged water | to 100 |

EXAMPLE 22

Water-in-Oil Emulsified Foundation (Method [1])

Volatile silicone, methylpolysiloxane, particulate titanium oxide, colorant, loading pigment and trimethyl siloxysilicic acid as oil phase constituent were dispersed by a disper in a batch media-agitating mill for 5 minutes, and then dispersed by the media mill part for 30 minutes. Thereafter, additive components and an water phase were added and the mixture was dispersed for 5 minutes by the disper, and then dispersed by the media mill part for 5 minutes whereby emulsifying the formulation.

(Method [2])

Volatile silicone, methylpolysiloxane, particulate titanium oxide, colorant, loading pigment and trimethyl siloxysilicic acid as oil phase constituent were dispersed by a disper in a preliminary stirring tank of a continuous media-agitating mill fitted with the preliminary stirring tank for 5 minutes, and then dispersed by subjecting to 3 passes in the media mill part. Thereafter, additive components and an water phase were added and the mixture was added to the preliminary stirring tank and dispersed for 5 minutes by the disper, and then subjected to 2 passes in the media mill part, whereby dispersing and emulsifying the formulation.

| (oil phase) | |
| --- | --- |
| volatile silicone | 20 |
| methylpolysiloxane | 15 |
| particulate titanium oxide (aluminum-treated) | 5 |
| organically-denatured bentonite | 1 |
| titanium oxide | 8 |
| yellow iron oxide | 2 |
| red iron oxide | 1 |
| black iron oxide | 0.5 |
| talc | 10 |
| trimethyl siloxysilicic acid | 4.5 |
| (adjucion components) | |
| nylone powder | 3 |
| polyoxyethylene-methylpolysiloxane copolymer | 2 |
| sorbitan sesqui isostearate | 1 |
| (water phase) | |
| moisturizing element | 8 |
| antiseptic | q.s. |
| sodium glutamate | 2 |
| ion-exchanged water | to 100 |

In a method for producing an emulsified cosmetic product involving a hydrophobicity-imparting step according to the invention, a production method using no organically-denatured clay mineral is possible as described in Example 23 shown below. However, a production method using an organically-denatured clay mineral described above is preferable for the purpose of ensuring the stability of cosmetic products.

EXAMPLE 23

Water-in-Oil Emulsified Foundation (Method [1])

Volatile silicone, methylpolysiloxane, particulate zinc oxide and trimethyl siloxysilicic acid as oil phase constituent were dispersed by a disper in a batch media-agitating mill for 5 minutes, and then dispersed by the media mill part for 30 minutes. Thereafter, additive components and an water phase were added and the mixture was dispersed for 5 minutes by the disper, and then dispersed by the media mill part for 5 minutes whereby emulsifying the formulation.

(Method [2])

Volatile silicone, methylpolysiloxane, particulate zinc oxide and trimethyl siloxysilicic acid as oil phase constituent were dispersed by a disper in a preliminary stirring tank of a continuous media-agitating mill fitted with the preliminary stirring tank for 5 minutes, and then dispersed by subjecting to 5 passes in the media mill part. Thereafter, additive components and an water phase were added and the mixture was added to the preliminary stirring tank and dispersed for 5 minutes by the disper, and then subjected to 1 pass in the media mill part, whereby dispersing and emulsifying the formulation.

| (oil phase) | |
| --- | --- |
| volatile silicone | 30 |
| methylpolysiloxane | 5 |
| particulate zinc oxide | 15 |
| trimethyl siloxysilicic acid | 4.5 |

| (adjucion components) | |
| --- | --- |
| silicone resin powder | 3 |
| octyl methoxy cinnamate | 7.5 |
| polyoxyethylene-methylpolysiloxane copolymer | 1 |
| isostearic acid | 0.5 |
| perfume | q.s. |
| (water phase) | |
| moisturizing element | 5 |
| antiseptic | q.s. |
| sodium glutamate | 1 |
| ion-exchanged water | to 100 |

<Method for Producing Lipstick>

The inventors subsequently investigated a method for producing a lipstick containing powder component of a colorant. A method for producing a lipstick according to the invention is described below.

Batch Media-Agitating Mill

A batch media-agitating mill which is a dispersing device employed in a method for producing a lipstick according to the invention is as described above.

Method for Producing Lipstick

In a concrete example of a method for producing a lipstick according to the invention, a batch media-agitating mill having a disper as an in-tank stirring device is used to mix oil components and colorant powders by the disper and then a basket part as a media mill part is used to disperse and mix the formulation, which is then supplemented with a wax if a solidifying agent is necessary, and melted by heating, and then filled into a certain mold to obtain a solid lipstick. According to an inventive method for producing a lipstick, a lipstick can be produced in a single tank within a short time at a low cost. A washing step after the production can also be simplified substantially when compared with a conventional method using a media-agitating mill. Moreover, a lipstick obtained according to the invention in which colorant powders have been ground and dispersed excellently exhibits an excellent gloss, can smoothly be extended, shows an excellent color development and is difficult to be broken.

Colorant Powder Components

A colorant powder component in the invention may, for example, be an inorganic powder such as titanium oxide, zinc oxide, red iron oxide, yellow iron oxide, black iron oxide, ultramarineblue, cerium oxide, talc, mica, sericite, kaolin, silica, zinc stearate, fluorine phlogopite, synthesis talc, barium sulfate, magnesium carbonate and boron nitride; an organic powder component such as nylon powder, polyethylene powder, silicone powder, silicone elastic powder, polyurethane powder, cellulose powder, PMMA powder, polyethylene powder; an inorganic white pigment such as titanium oxide and zinc oxide; an inorganic colored pigment such as red iron oxide, yellow iron oxide, black iron oxide, carbon black, manganese violet, cobalt violet, ultramarineblue and prussian blue; a pearl pigment such as titanium oxide coated mica, titanium oxide coated talc, coloring titanium oxide coated mica, bismuth oxychloride and scale powder; a metal powder pigment such as alumina; an organic pigment such as zirconium, barium or aluminium lake including red No. 201, red No. 202, red No. 204, red No. 205, red No. 220, red No. 226, red No. 228, red No. 305, bitter orange No. 203, bitter orange No. 204, yellow No.

205, yellow No. 401, blue No. 404, red No. 3, red No. 104, red No. 106, red No. 227, red No. 230, red No. 401, red No. 505, bitter orange No. 205, yellow No. 4, yellow No. 5, yellow No. 202 and yellow No. 203. Powder obtained by treating the surface of any powder described above with silicone, fluorine, teflon, fatty acids, fatty acid soaps, lauroyllysine and the like may also be employed. One or more of these powders are added preferably in an amount of 1 to 60% by weight.

Colorant Particulate Powder Components

A colorant powder component in the invention may, for example, be a particulate colorant powder whose mean particle size is 0.005 to 0.5 μm. Such particulate colorant powder may, for example, be particulate titanium oxide, particulate zinc oxide, particulate red iron oxide, particulate yellow iron oxide, particulate black iron oxide, particulate cobalt blue and the like. A particulate colorant powder is known to be more excellent in the color tone such as the transparency when compared with an ordinary colorant. When a particulate colorant is incorporated, one or more such colorants are present preferably in an amount of 1 to 20% by weight in 1 to 60% by weight of the colorant components. An amount less than 1% by weight may lead to a difficulty in developing the color of the particulate colorant sufficiently, while an amount exceeding 20% by weight presents a large specific surface area of the particulate colorant powder which leads to a poor the inventorsttability in oil components, resulting in a dusty skin feel and a poor moldability.

Oil Components

As an oil component in the invention, any of those employed in the method for producing the cosmetic products containing the particulate powder components described above can be employed. The oil components are present preferably in an amount of 25 to 90% by weight in total.

Wax Components

When producing a solid lipstick according to the invention, a wax component is preferably incorporated as a solidifying agent. A wax component as a solidifying agent may, for example, be microcrystalline wax, carnauba wax, candelilla wax, polyethylene wax, ceresin wax and the like, which may be used in combination. The wax components, when added to produce a lipstick, are contained preferably in an amount of 3 to 25% by weight in total.

Other Components

A lipstick formulation according to the invention may further contain surfactants, dispersants, stabilizers, other colorants, antiseptics, antioxidants, UV absorbers, perfumes and the like appropriately as long as the objectives of the invention are accomplished.

The present invention is further described in Examples, which are not intended to restrict the invention.

The invention can preferably be applied to the production of a lipstick containing 1 to 60% by weight of colorant powder components, 25 to 90% by weight of oil components and 3 to 25% by weight of wax components. Concrete examples are described below. The evaluation of practical characteristics was performed as detailed below.

Evaluation of Practical Characteristics

20 Female panelists received the application of a test formulation and evaluated the formulation with regard to the extending performance, the gloss and the breaking resistance as well as the transparency of some of the formulations.

<Evaluation>

| | |
|---|---|
| 17 Panelists or more judged as good. | A |
| 12 to 16 Panelists judged as good. | B |
| 9 to 11 Panelists judged as good. | C |
| 5 to 8 Panelists judged as good. | D |
| 4 Panelists or less judged as good. | E |

Evaluation of Lipstick Color Tone (Chorma and Brightness)

A melted lipstick base was cast into a glass cell and cooled to solidify, and then measured by a spectrophotometer.

EXAMPLE 24

COMPARATIVE EXAMPLE 17

Oily Lipstick

Table 28 shows an oily lipstick as Example 24 produced by a production method of the invention. The colorant powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes. Wax components were added and the tank was heated to 90 to 95° C., and then the formulation was cast as melted into a lipstick mold, which was cooled to obtain a lipstick. On the other hand, Comparative example 17 employed an ordinary production method. The colorant powder components in the formulation identical to that in Example 24 and a part of the oil components were kneaded in a roll mill to form a slurry, which was added to a melted mixture of other oil components and the wax components in the tank, mixed by a homogenizer, and molded into a lipstick by a method similar to that in Example 24.

TABLE 28

| Oily lip stick | Example 24 | Comparative example 17 |
|---|---|---|
| ceresin wax | 12 | 12 |
| polyethylene wax | 5 | 5 |
| liquid paraffin | 30 | 30 |
| glycelyl tri-octanoate | to 100 | to 100 |
| glycelyl di-stearate | 15 | 15 |
| dimethylpolysiloxane | 15 | 15 |
| red iron oxide | 4 | 4 |
| yellow iron oxide | 0.5 | 0.5 |
| black iron oxide | 0.5 | 0.5 |
| pearl element | 5 | 5 |
| antioxidant | q.s. | q.s. |
| perfume | q.s. | q.s. |
| extending performance | A | B |
| smoothness | A | B |
| breaking resistance | A | B |
| chroma | 6.2 | 5.5 |
| brightness | 5.2 | 4.7 |

As evident from the results shown in Table 28, the lipstick (Example 24) obtained by a production method employing a batch media-agitating mill according to the invention was excellent in the skin touch and the color development (chroma and brightness) because of a satisfactorily dispersed colorant powders such as yellow iron oxide and black iron oxide. On the contrary, the lipstick (Comparative example 17) produced only by an ordinary dispersing device such as a homogenizer was poor in terms of the skin touch and the color development when compared with the inventive lipstick because of insufficiently dispersed colorant powders described above.

EXAMPLE 25

COMPARATIVE EXAMPLE 18-1, 18-2

Lipstick

Table 29 shows an oily lipstick as Example 25 containing particulate colorant powders which was produced by a production method of the invention. The colorant powder component and the oil components in the formulation indicated below were mixed for 10 minutes by a disper fitted in a batch media-agitating mill, and then a basket part containing zirconia beads each in 1 mm in diameter was driven to disperse and mix the formulation for 30 minutes. Wax components were added and the tank was heated to 90 to 95° C., and then the formulation was cast as melted into a lipstick mold, which was cooled to obtain a lipstick. On the other hand, each of Comparative example 18-1 and 18-2 employed an ordinary production method. In Comparative example 18-1, the colorant powder components and the oil components in the formulation identical to that in Example 25 were mixed by a disper for 10 minutes and the colorant powder components were added to the melted wax components in the tank, dispersed and mixed by a homogenizer for 30 minutes, and molded into a lipstick by a method similar to that in Example 25. In Comparative example 18-2, the colorant powder components in the formulation identical to that in Example 25 and a part of the oil components were mixed by a disper for 10 minutes and then ground and dispersed in a roll mill to form a paste composition, which was added to a melted mixture of other oil components and the wax components in the tank, dispersed and mixed by a homogenizer for 10 minutes, and molded into a lipstick by a method similar to that in Example 25.

TABLE 29

| Lip stick | Example 25 | Comparative example 18-1 | Comparative example 18-2 |
|---|---|---|---|
| ceresin wax | 12 | 12 | 12 |
| polyethylene wax | 3 | 3 | 3 |
| liquid paraffin | 30 | 30 | 30 |
| glycelyl tri-octanoate | to 100 | to 100 | to 100 |
| glycelyl di-stearate | 15 | 15 | 15 |
| dimethylpolysiloxane | 15 | 15 | 15 |
| particulate red iron oxide | 4 | 4 | 4 |
| particulate yellow iron oxide | 2 | 2 | 2 |
| particulate black iron oxide | 1 | 1 | 1 |
| antioxidant | q.s. | q.s. | q.s. |
| perfume | q.s. | q.s. | q.s. |
| extending performance | A | C | B |
| smoothness | A | C | B |
| breaking resistance | A | C | B |
| transparency | A | D | C |
| chroma | 8.2 | 3.9 | 6.7 |
| brightness | 4.9 | 6.7 | 5.1 |

As evident from the results shown in Table 29, the lipstick (Example 25) obtained by a production method employing a batch media-agitating mill according to the invention was excellent in the skin touch, the color development (chroma and brightness) and the transparency because of a satisfactorily dispersed particulate colorant powders which were particulate red iron oxide, particulate yellow iron oxide and particulate black iron oxide. On the contrary, the lipsticks (Comparative example 18-1 and 18-2) produced only by ordinary dispersing devices such as a disper and a homogenizer were poor in terms of the skin touch, the color development and the transparency when compared with the inventive lipstick because of insufficiently dispersed particulate colorant powders described above, thus being unsuccessful in exerting the characteristics of the particulate colorant powders as the coloring agents.

What is claimed is:

1. A method for producing solid powdery cosmetic products comprising a step wherein powder components and oil components as binders are mixed in a solvent using a media-agitating mill to form a slurry and wherein grinding of the powder components and depositing oil components uniformly over the surface of powder components are performed simultaneously using a media-agitating mill.

2. A method for producing cosmetic products according to claim 1 further comprising a step wherein the slurry is made free from the solvent and filled in a container.

3. A method for producing cosmetic products according to claim 1 further comprising a step wherein the slurry is made free from the solvent and filled in a container and then subjected to a dry press molding.

4. A method for producing cosmetic products according to claim 1 further comprising a step wherein the slurry is filled in a container and then subjected to a suction press molding.

5. A method for producing cosmetic products according to claim 1 wherein the solid powdery cosmetic product comprises 65 to 97% by weight of the powder components and 3 to 35% by weight of the oil components.

6. A method for producing powdery cosmetic products comprising a step wherein powder components, oil components and organic silicon resin compounds are mixed in a solvent to form a slurry and wherein and hydropbobing of powder components are performed simultaneously using a media-agitating mill.

7. A method for producing cosmetic products according to claim 6 wherein the powdery cosmetic product contains 60 to 97% by weight of powder components, 1 to 20% by weight of a particle coating agent and 2 to 30% by weight of oil components.

8. A method for producing cosmetic products comprising the following steps of (A)–(C) using a batch media-agitating mill, wherein said batch media-agitating mill comprises, in an identical tank,
   at least one basket part which has an in-basket stirring device for stirring the content of the basket and wherein solid dispersion and medium are contained and,
   at least one in-tank stirring device wherein said in-tank stirring device is provided in a position which does not interfere with the route of a fluid coming into and out of the basket part:
   (A) materials containing powder components are mixed by the in-tank stirring device and run into the basket part;
   (B) after (A), the powder components are ground and dispersed by the solid dispersion medium in the basket part and then run out of the basket part as a dispersion;
   (C) after (B), the dispersion runs into the basket part by the in-tank stirring device and circulates in the batch media-agitating mill.

9. A method for producing cosmetic products according to claim 8 wherein a side wall or a side wall and a bottom wall of said basket part are provided with a large number of small pores each consisting of a slit whose size does not allow the solid dispersion medium to run out of the basket part.

10. A method for producing cosmetic products according to claim 8 wherein said in-tank stirring device for both of a preliminary mixing and a dispersion fluidization employs a disper or a homogenizer having a turbinal blade on the tip of a rotating rod or a combination thereof.

11. A method for producing solid oily cosmetic products comprising a step wherein powder components and oil components are mixed using a media-agitating mill, wherein grinding and dispersing of the powder components into the oil components are performed simultaneously using a media-agitating mill, wherein followed by an addition of a solidifying aid followed by a stirring with heating followed by a compaction molding.

12. A method for producing cosmetic products comprising a step wherein powder components and oil components are mixed using a media-agitating mill, wherein grinding and dispersing of the powder components to the oil components are performed simultaneously using a media-agitating mill wherein followed by an addition of the aqueous components and wherein emulsification is by using a media-agitating mill.

13. A method for producing cosmetic products comprising a step wherein organically-denatured clay minerals, surfactants, hydrophobic dispersion medium capable of dispersing and swelling said organically-denatured clay minerals in the presence of surfactants, particles which are not made hydrophobic and particle coating agents are mixed using a media-agitating mill wherein grinding and hydrophobing of the powder components are performed simultaneously using a media-agitating mill.

14. A method for producing cosmetic products according to claim 13 comprising a step for mixing an organically-denatured clay mineral, a surfactant and a hydrophobic dispersion medium to form an organically-denatured clay mineral dispersion, adding a particle which is not made hydrophobic and a particle coating agent to said organically-denatured clay mineral dispersion and mixing using a media-agitating mill to impart the surface of said particle with a hydrophobicity.

15. A method for producing cosmetic products according to claim 13 wherein the concentration of the organically-denatured clay mineral when mixing using a media-agitating mill ranges from 0.1 to 5% by weight.

16. A method for producing cosmetic products according to claim 13 wherein the concentration of the particle which is not made hydrophobic when mixing using a media-agitating mill ranges from 5 to 50% by weight.

17. A method for producing cosmetic products according to claim 13 wherein the particle coating agent is trimethylsiloxysilicic acid.

18. A method for producing cosmetic products according to claim 13 wherein the particle which is not made hydrophobic is a UV-protecting particle.

19. A method for producing cosmetic products according to claim 18 wherein the UV-protecting particle is one or more selected from the group consisting of zinc oxide, iron oxide, cerium oxide and titanates.

20. A method for producing emulsified cosmetic products comprising a step wherein powder components which are not made hydrophobic and oil components are mixed using a media-agitating mill, wherein dispersing and hydrophobing of the not made hydrophobic powder components are performed simultaneously using a media-agitating mill, and followed by a step wherein an emulsifier and a water phase are added and emulsified using a media mill.

21. A method for producing cosmetic products according to claim 20 wherein the device is a batch media-agitating mill having a media mill part and a stirring device in a single tank.

22. A method for producing cosmetic products according to claim 20 wherein the device is a continuous media-agitating mill consisting of a media mill part and a preliminary stirring tank and whose media mill part is connected via a pipe with the preliminary stirring tank.

23. A method for producing cosmetic products according to claim 20 wherein the emulsified cosmetic product is of a water-in-oil material.

24. A method for producing solid lipstick cosmetic products comprising a step wherein powder components of a colorant and oil components are mixed in a solvent using a media-agitating mill, wherein grinding and dispersing the powder components to the oil components are performed simultaneously using a media-agitating mill, and wherein followed by an addition of a solidifying aid followed by a stirring with heating followed by a compaction molding.

25. A method for producing emulsified cosmetic products comprising a step wherein powder components and aqueous components are mixed using a media-agitating mill, wherein grinding and dispersing of the powder components to the aqueous components are performed simultaneously using a media-agitating mill, wherein followed by an addition of the oil components and wherein emulsified by using a media-agitating mill.

* * * * *